US008895509B2

(12) United States Patent
McDonald et al.

(10) Patent No.: US 8,895,509 B2
(45) Date of Patent: Nov. 25, 2014

(54) MIR-200 FAMILY INDUCES MESENCHYMAL-TO-EPITHELIAL TRANSITION (MET) IN OVARIAN CANCER CELLS

(75) Inventors: John McDonald, Arnoldsville, GA (US); Nathan John Bowen, Atlanta, GA (US); LiJuan Wang, Smyrna, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 13/989,312

(22) PCT Filed: Nov. 23, 2011

(86) PCT No.: PCT/US2011/062004
§ 371 (c)(1),
(2), (4) Date: May 23, 2013

(87) PCT Pub. No.: WO2012/071492
PCT Pub. Date: May 31, 2012

(65) Prior Publication Data
US 2013/0243876 A1 Sep. 19, 2013

Related U.S. Application Data

(60) Provisional application No. 61/416,434, filed on Nov. 23, 2010.

(51) Int. Cl.
| A61K 48/00 | (2006.01) |
| A61K 9/51 | (2006.01) |
| A61K 45/06 | (2006.01) |
| A61K 31/713 | (2006.01) |
| A61K 31/7105 | (2006.01) |
| C12N 15/113 | (2010.01) |
| A61K 9/00 | (2006.01) |

(52) U.S. Cl.
CPC ....... *A61K 31/7105* (2013.01); *C12N 2310/141* (2013.01); *A61K 9/51* (2013.01); *A61K 45/06* (2013.01); *A61K 31/713* (2013.01); *A61K 9/5138* (2013.01); *C12N 15/113* (2013.01); *A61K 9/00* (2013.01)
USPC ............................................ 514/14; 536/24.5

(58) Field of Classification Search
CPC combination set(s) only.
See application file for complete search history.

(56) References Cited

U.S. PATENT DOCUMENTS

| 5,516,631 | A | 5/1996 | Frisch | |
| 2009/0163435 | A1* | 6/2009 | Bader et al. ............... | 514/44 |
| 2010/0088775 | A1 | 4/2010 | Khew-Goodall et al. | |
| 2011/0021607 | A1 | 1/2011 | Clarke et al. | |
| 2011/0091562 | A1* | 4/2011 | Lyon et al. ............... | 424/491 |

FOREIGN PATENT DOCUMENTS

| EP | 2341145 | 7/2011 |
| WO | WO 2008/036765 A2 | 3/2008 |
| WO | WO 2008/138578 | 11/2008 |
| WO | WO 2009/036332 A1 | 3/2009 |
| WO | WO 2009/097136 A1 | 8/2009 |
| WO | WO 2009/100430 A2 | 8/2009 |
| WO | WO 2009/143379 A2 | 11/2009 |
| WO | WO 2010/005741 A1 | 1/2010 |
| WO | WO 2010/048123 | 4/2010 |
| WO | WO 2010/056737 A2 | 5/2010 |
| WO | WO 2011/088226 A2 | 7/2011 |
| WO | WO 2011/099007 A1 | 8/2011 |
| WO | WO 2011/106709 A2 | 9/2011 |

OTHER PUBLICATIONS

Cochrane et al. (J. Oncology 2010, 821717, pp. 1-12).*
Park et al. (Genes Dev. 2008, vol. 22 894-907).*
van Jaarsveld et al. (Int. J. of Biochem & Cell Bio 2010 1282-1290).*
Hu et al. (Gynecologic Oncology 2009, vol. 114: 457-464).*
Bendoraite et al. "Regulation of miR-200 Family microRNAs and SEB Transcription Factors in Ovarian Cancer: Evidence Supporting a Mesothelial-to-Epithelial Transition" *Gynecologic Oncology* 2010, 116(1): 117-125.
Cochrane et al. "MicroRNA-200c Mitigates Invasiveness and Restores Sensitivity to Microtubule-Targeting Chemotherapeutic Agents" *Molecular Cancer Therapeutics* 2009, 8:1055-1066.
Cochrane et al. "Loss of miR-200c: A Marker of Aggressiveness and Chemoresistance in Female Reproductive Cancers" *Journal of Oncology* 2010, 2010:1-12.
Dickerson et al. "Chemosensitization of Cancer Cells by siRNA Using Targeted Nanogel Delivery" *BMC Cancer* 2010, 10(10):1-11.
Frenster et al. "Reprogramming the Human Cancer Cell Nucleus" *Genome Biology* 2010, 11(Suppl 1):P14.
Frisch. "Reprogramming Breast Cancer Epithelial Cells" California Breast Cancer Research Program 1997 (Abstract and Final Report) (1 page).
Gregory et al. "The miR-200 Family and miR-205 Regulate Epithelial to Mesenchymal Transition by Targeting ZEB1 and SIP1" *Nature Cell Biology* 2008, 10(5):593-601 ((Supplementary Information pp. 1-7).
Gregory et al. "MicroRNAs Regulators of Epithelial-mesenchymal Transition" *Cell Cycle* 2008, 7(20):3112-3117.
Hu et al. "A miR-200 microRNA Cluster as Prognostic Marker in Advanced Ovarian Cancer" *Gynecologic Oncology* 2009, 114:457-464.

(Continued)

*Primary Examiner* — Kimberly Chong
(74) *Attorney, Agent, or Firm* — Myers Bigel Sibley & Sajovec, PA

(57) ABSTRACT

The present invention provides a method of treating an ovarian cancer, the method comprising delivering one or more miR-200 family members to a mammalian subject in need thereof in an amount effective to treat the ovarian cancer. Also provided are methods of preventing metastasis of an ovarian cancer, the method comprising delivering one or more miR-200 family members to a mammalian subject in need thereof in an amount effective to prevent metastasis. Further provided are methods of sensitizing an ovarian cancer to a cytotoxic therapy, the method comprising delivering one or more miR-200 family members to a mammalian subject in need thereof in an amount effective to sensitize the ovarian cancer to the cytotoxic therapy. The invention also contemplates methods of reducing epithelial-to-mesenchymal transition (EMT) in an ovarian cancer or cancer cell as well as methods of inducing mesenchymal-to-epithelial transition (MET).

14 Claims, 5 Drawing Sheets

(56) References Cited

OTHER PUBLICATIONS

International Search Report and Written Opinion for International Application No. PCT/US2011/62004; Date of Mailing: Mar. 16, 2012; 9 Pages.

Korpal et al. "The miR-200 Family Inhibits Epithelial-Mesenchymal Transition and Cancer Cell Migration by Direct Targeting of E-cadherin Transcriptional Repressors ZEB1 and ZEB2" *Journal of Biological Chemistry* 2008, 283(22):14910-14914.

Lin et al. "Mir-302 Reprograms Human Skin Cancer Cells into a Pluripotent ES-cell-like State" *RNA* 2008, 14:2115-2124.

Mueller et al. "Terminal Differentiation of Human Breast Cancer through PPAR" *Molecular Cell* 1998, 1:465-470.

Okuyama et al. "Redifferentiation of Cancer Cells: Bestatin, Estradiol, and Prostaglandin $D_2$" *Annals New York Academy of Sciences* 1985, 459:293-307.

Park et al. The miR-200 Family Determines the Epithelial Phenotype of Cancer Cells by Targeting the E-cadherin Repressors ZEB1 and ZEB2, Genes & Development 2008, 22: 894-907.

Paterson et al. "The microRNA-200 Family Regulates Epithelial to Mesenchymal Transition" *The Scientific World Journal* 2008, 8:901-904.

Sakagami et al. "Apoptosis-Inducing Activity of Vitamin C and Vitamin K" *Cellular and Molecular Biology* 2000, 46:129-143 (Abstract Only).

Sultan et al, "Co-Overexpression of Janus kinase 2 and Signal Transducer and Activator of Transcription 5a Promotes Differentiation of Mammary Cancer Cells through Reversal of Epithelial-mesenchymal Transition" *Cancer Science* 2008, 99(2):272-279.

Sun et al. "Effect of Collagen Type II on Redifferentiation of Dedifferentiated Rabbit Chondrocytes" *Chinese Journal of Reparative and Reconstructive Surgery* 2010, 24(10):1244-1248.

Yaccoby. "The Phenotypic Plasticity of Myeloma Plasma Cells as Expressed by Dedifferentiation into an Immature, Resilient, and Apoptosis-Resistant Phenotype" *Human Cancer Biology* 2005, 11(21):7599-7606.

* cited by examiner

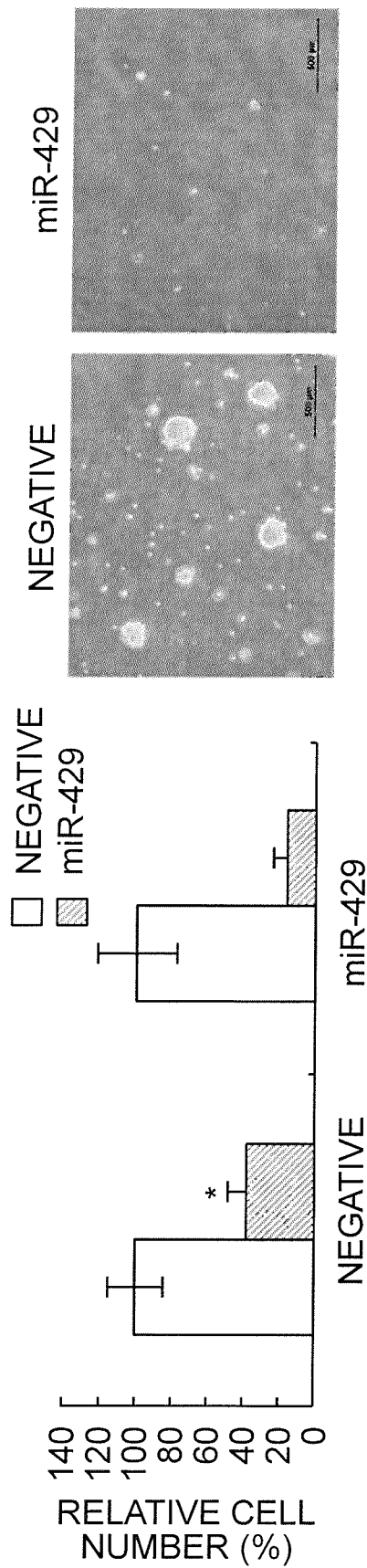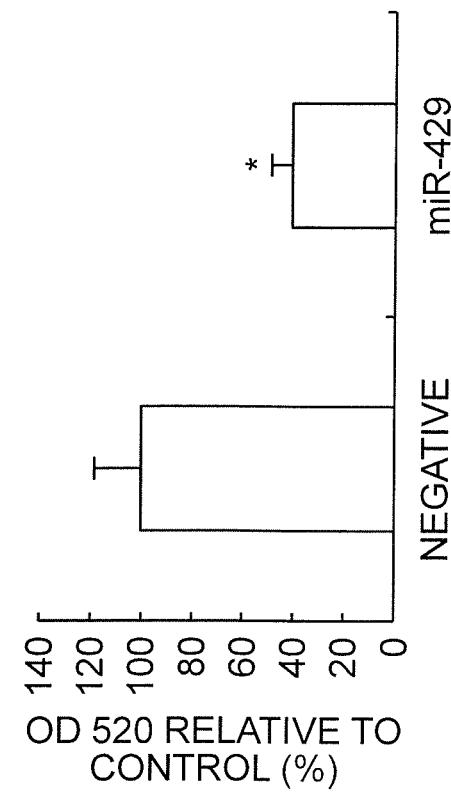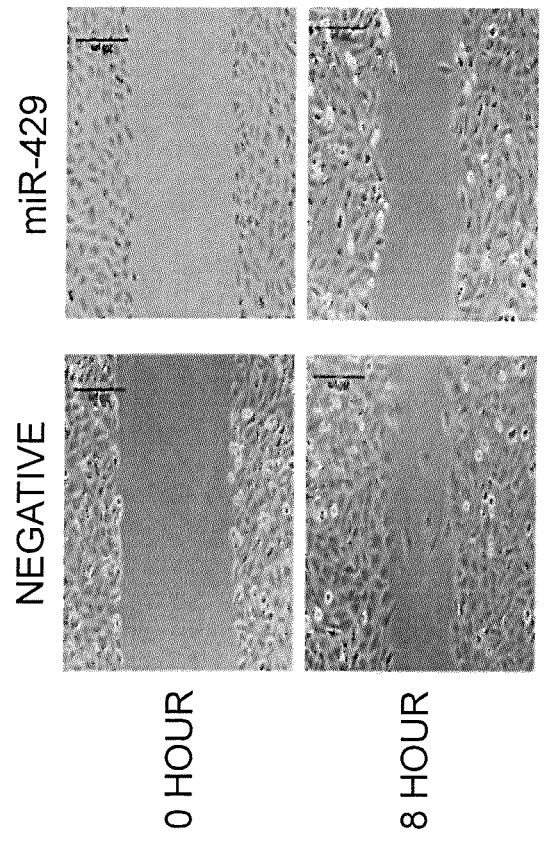
FIG. 4A
FIG. 4C
FIG. 4B

*ERROR BARS REPRESENT S.E.M. OF THE MEAN IC50 OF THREE REPLICATES.

```
                       SEQUENCE LISTING

<160> NUMBER OF SEQ ID NOS: 11

<210> SEQ ID NO 1
<211> LENGTH: 95
<212> TYPE: RNA
<213> ORGANISM: Homo sapiens

<400> SEQUENCE: 1
ccagcucggg cagccguggc caucuuacug ggcagcauug gauggaguca ggucucuaau      60
acugccuggu aaugaugacg gcggagcccu gcacg                                 95

<210> SEQ ID NO 2
<211> LENGTH: 22
<212> TYPE: RNA
<213> ORGANISM: Homo sapiens

<400> SEQUENCE: 2
uaauacugcc ugguaaugau ga                                               22

<210> SEQ ID NO 3
<211> LENGTH: 68
<212> TYPE: RNA
<213> ORGANISM: Homo sapiens

<400> SEQUENCE: 3
cccucgucuu acccagcagu guuuggguge gguugggagu cucuaauacu gccgggguaau     60 gauggagg                                                               68

<210> SEQ ID NO 4
<211> LENGTH: 23
<212> TYPE: RNA
<213> ORGANISM: Homo sapiens

<400> SEQUENCE: 4
uaauacugcc ggguaaugau gga                                              23

<210> SEQ ID NO 5
<211> LENGTH: 83
<212> TYPE: RNA
<213> ORGANISM: Homo sapiens
```

```
<400> SEQUENCE: 5
cgccggccga ugggcgucuu accagacaug guuagaccug gcccucuguc uaauacuguc    60
ugguaaaacc guccauccgc ugc                                           83

<210> SEQ ID NO 6
<211> LENGTH: 22
<212> TYPE: RNA
<213> ORGANISM: Homo sapiens

<400> SEQUENCE: 6
uaauacuguc ugguaaaacc gu                                            22

<210> SEQ ID NO 7
<211> LENGTH: 95
<212> TYPE: RNA
<213> ORGANISM: Homo sapiens

<400> SEQUENCE: 7
cggccggccc uggguccauc uuccaguaca guguuggaug gucuaauugu gaagcccua    60 acacugucug guaaagaugg cucccggguc gguuc                              95

<210> SEQ ID NO 8
<211> LENGTH: 22
<212> TYPE: RNA
<213> ORGANISM: Homo sapiens

<400> SEQUENCE: 8
uaacacuguc ugguaaagau gg                                            22

<210> SEQ ID NO 9
<211> LENGTH: 90
<212> TYPE: RNA
<213> ORGANISM: Homo sapiens

<400> SEQUENCE: 9 ccgggcccu gugagcaucu uaccggacag ugcuggauuu cccagcuuga cucuaacacu    60
gucugguaac gauguucaaa ggugacccgc                                    90

<210> SEQ ID NO 10
<211> LENGTH: 22
<212> TYPE: RNA
<213> ORGANISM: Homo sapiens

<400> SEQUENCE: 10
uaacacuguc ugguaacgau gu                                            22

<210> SEQ ID NO 11
<211> LENGTH: 13
<212> TYPE: PRT
<213> ORGANISM: Artificial
<220> FEATURE:
<223> OTHER INFORMATION: EphA2 receptor targeting sequence

<400> SEQUENCE: 11

Tyr Ser Ala Tyr Pro Asp Ser Val Pro Met Met Ser Cys
1               5                   10
```

US 8,895,509 B2

MIR-200 FAMILY INDUCES MESENCHYMAL-TO-EPITHELIAL TRANSITION (MET) IN OVARIAN CANCER CELLS

RELATED APPLICATION INFORMATION

This application is a 35 U.S.C. §371 national phase application of International Application Serial No. PCT/US2011/062004, filed Nov. 23, 2011, which claims the benefit of U.S. Provisional Application No. 61/416,434, filed Nov. 23, 2010, the disclosures of each of which are incorporated by reference herein in their entireties.

STATEMENT REGARDING ELECTRONIC FILING OF A SEQUENCE LISTING

A Sequence Listing in ASCII text format, submitted under 37 C.F.R. §1,821, entitled 9844-14TS_ST25.txt, 2,469 bytes in size, generated on May 23, 2013 and filed via EFS-Web, is provided in lieu of a paper copy. This Sequence Listing is hereby incorporated by reference into the specification for its disclosures.

FIELD OF THE INVENTION

The present invention relates to miRNAs, in particular, the use of miRNAs to reduce epithelial-to-mesenchymal transition, to induce mesenchymal-to-epithelial transition, to treat ovarian cancer, to prevent metastasis of ovarian cancer and/or to sensitize ovarian cancer cells to cytotoxic agents.

BACKGROUND OF THE INVENTION

Ovarian cancer is a highly metastatic disease with the highest mortality rate of all gynecologic cancers, and is typically not diagnosed until advanced stages of the disease [Jemal et al., CA Cancer J Clin 2008, 5:71-96]. While existing methodologies (surgery, radiation, chemotherapy) are considered relatively effective in the treatment of primary ovarian tumors, most patients treated for advanced-staged disease will eventually suffer recurrence at metastatic sites. Metastasis of ovarian and other cancers is promoted by the epithelial-to-mesenchymal transition (EMT) of primary tumor cells [Ahmed et al., J Cell Physiol 2007, 21:581-8; Zavadil et al., Cancer Res 2008, 68:9574-7; Iwatsuki et al., Cancer Sci 2009, 101:293-9; Thiery et al., Cell 2009, 139:871-90; Vergara et al. Cancer Lett 2010, 291:59-66]. Because metastasis is the major cause of all cancer related deaths, there is a need in the art to understand the molecular basis of the EMT to identify targets for therapeutic intervention.

SUMMARY OF THE INVENTION

Ovarian cancer is the most lethal of all gynecological malignancies primarily due to the sloughing-off of highly metastatic cells from primary tumors and their subsequent spread throughout the peritoneal cavity. The epithelial-to-mesenchymal transition (EMT) of ovarian cancer cells located at the periphery of the primary tumor is believed to be a precursor to metastasis. These mesenchymal-like cells are only slowly dividing, or even non-dividing, and are not good targets for current cytotoxic therapies. The present invention is based, in part, on the discovery that over-expression of members of the miR-200 family in ovarian cancer cells with a mesenchymal phenotype induced mesenchymal-to-epithelial transition (MET) and sensitized the cells to treatment with a cytotoxic agent.

Accordingly, as one aspect, the present invention provides a method of treating an ovarian cancer, the method comprising delivering one or more miR-200 family members to a mammalian subject in need thereof in an amount effective to treat the ovarian cancer.

The invention also provides a method of preventing metastasis of an ovarian cancer, the method comprising delivering one or more miR-200 family members to a mammalian subject in need thereof in an amount effective to prevent metastasis. According to this aspect, in a subject with localized disease, future metastasis can be prevented. In a subject that has, or has had, metastatic disease, the invention can be practiced to prevent further metastasis and spread.

As another aspect, the invention provides a method of sensitizing an ovarian cancer to a cytotoxic therapy (e.g., reducing resistance or refractoriness to a cytotoxic agent), the method comprising delivering one or more miR-200 family members to a mammalian subject in need thereof in an amount effective to sensitize the ovarian cancer to the cytotoxic therapy. The invention also contemplates methods of sensitizing an ovarian cancer cell to a cytotoxic therapy, the method comprising delivering one or more miR-200 family members to the ovarian cancer cell in an amount to sensitize the cell to the cytotoxic therapy.

Also encompassed by the present invention is a method of reducing epithelial-to-mesenchymal transition in an ovarian cancer, the method comprising delivering one or more miR-200 family members to a mammalian subject in need thereof in an amount effective to reduce epithelial-to-mesenchymal transition in the ovarian cancer. The invention can further be practiced to reduce epithelial-to-mesenchymal transition of an ovarian cancer cell, the method comprising delivering one or more miR-200 family members to an ovarian cancer cell (e.g., having an epithelial phenotype) in an amount effective to reduce epithelial-to-mesenchymal transition by the cell.

As still a further aspect, the invention provides a method of inducing mesenchymal-to-epithelial transition in an ovarian cancer, the method comprising delivering one or more miR-200 family members to a mammalian subject in need thereof in an amount effective to induce mesenchymal-to-epithelial transition in the ovarian cancer. Yet further, the invention provides a method of inducing mesenchymal-to-epithelial transition by an ovarian cancer cell, the method comprising delivering one or more miR-200 family members to an ovarian cancer cell (e.g., having a mesenchymal phenotype) in an amount effective to induce mesenchymal-to-epithelial transition by the cell.

In representative embodiments, the ovarian cancer or ovarian cancer cell is an epithelial ovarian cancer or epithelial ovarian cancer cell.

The foregoing and other aspects of the present invention will now be described in more detail in the following description of the invention.

Consistent with morphological differences, the mesenchymal markers VIM, FN1 and N-cadherin are all significantly (*p<0.01, t-test) more highly expressed in HEY cells relative to OVCAR3 cells; the epithelial marker E-cadherin is expressed at significantly lower levels (*p<0.01) while the repressors of E-cadherin, ZEB 1 and ZEB 2 are expressed at significantly higher levels (*p<0.01) in HEY relative to OVCAR3 cells. (C) Consistent with the hypothesis that the down-regulation of members of the miRNA-200 family of microRNAs may contribute to EMT in ovarian cancer, miR-141, miR-429 and miR-205 are all expressed at significantly lower levels (*p<0.01) in HEY relative to OVCAR3 cells while levels of 3 microRNAs not previously implicated in EMT (let-7a, let-7d and miR-320) are not significantly different between the two cell lines. The levels of mRNA shown in (B) and (C) were determined by qRT-PCR and the results reported as mean±SEM.

Figure 2A:
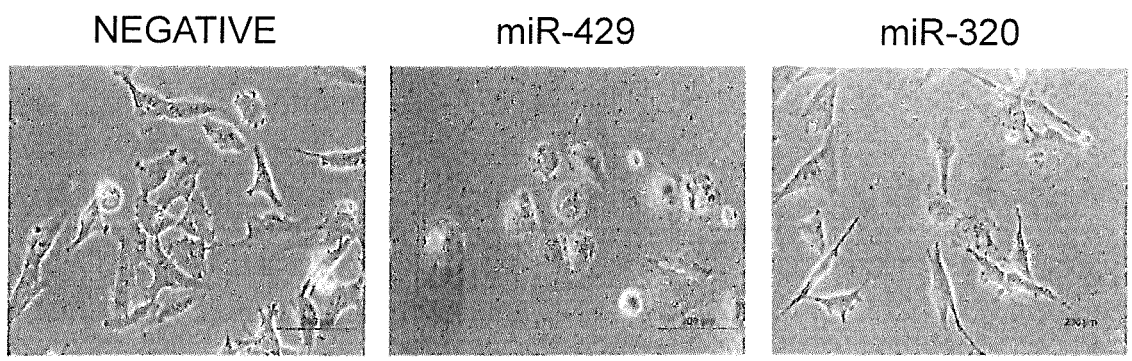
Figure 2B:
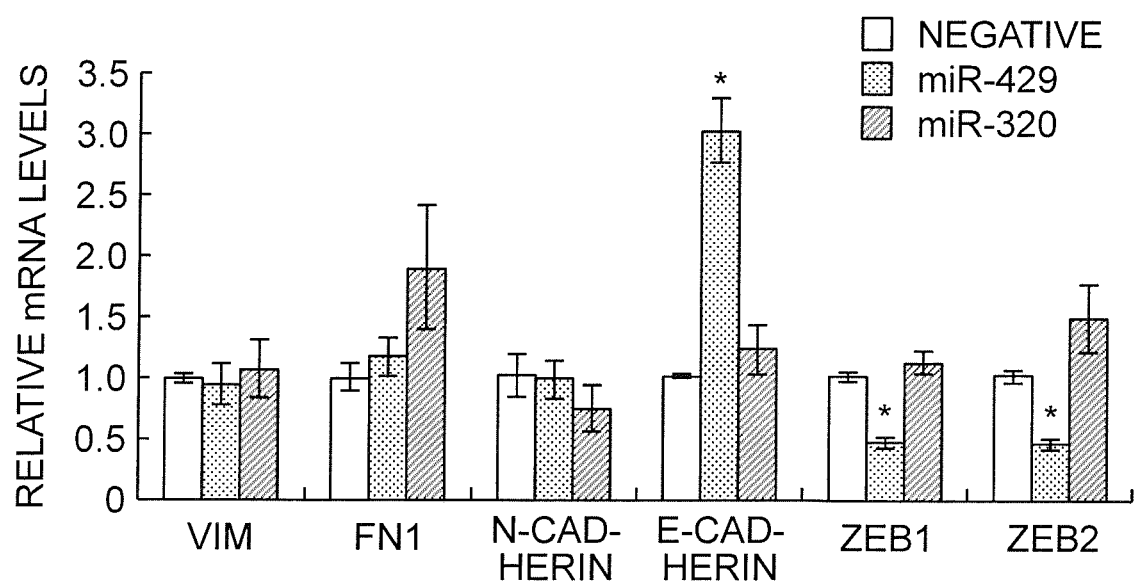

FIGS. 2A-B. Overexpression of miR-429 in HEY cells induces morphological and molecular changes characteristic of MET. (A) Cells transfected with miR-429 displayed a change from an elongated mesenchymal-like morphology to a rounded epithelial-like morphology. No morphological changes were observed in cells transfected with miR-320 or with the negative control. (B) Relative expression of mRNAs encoding ZEB2, ZEB1, E-cadherin, N-cadherin, FN1 (fibronectin) and VIM (vimentin) in HEY cells after transfection with miR-429, miR-320 and a negative control as determined by qRT-PCR. The data are reported as mean±SEM, Concurrent with the morphological changes, levels of ZEB1 and ZEB2 were significantly lower while levels of E-cadherin were significantly higher (*p<0.01) in cells transfected with miR-429 relative to cells transfected with miR-320 or the negative control. No significant difference in levels of VIM, FN1 and N-cadherin were detected among cells transfected with miR-429, miR-320 or the negative control.

Figure 3:
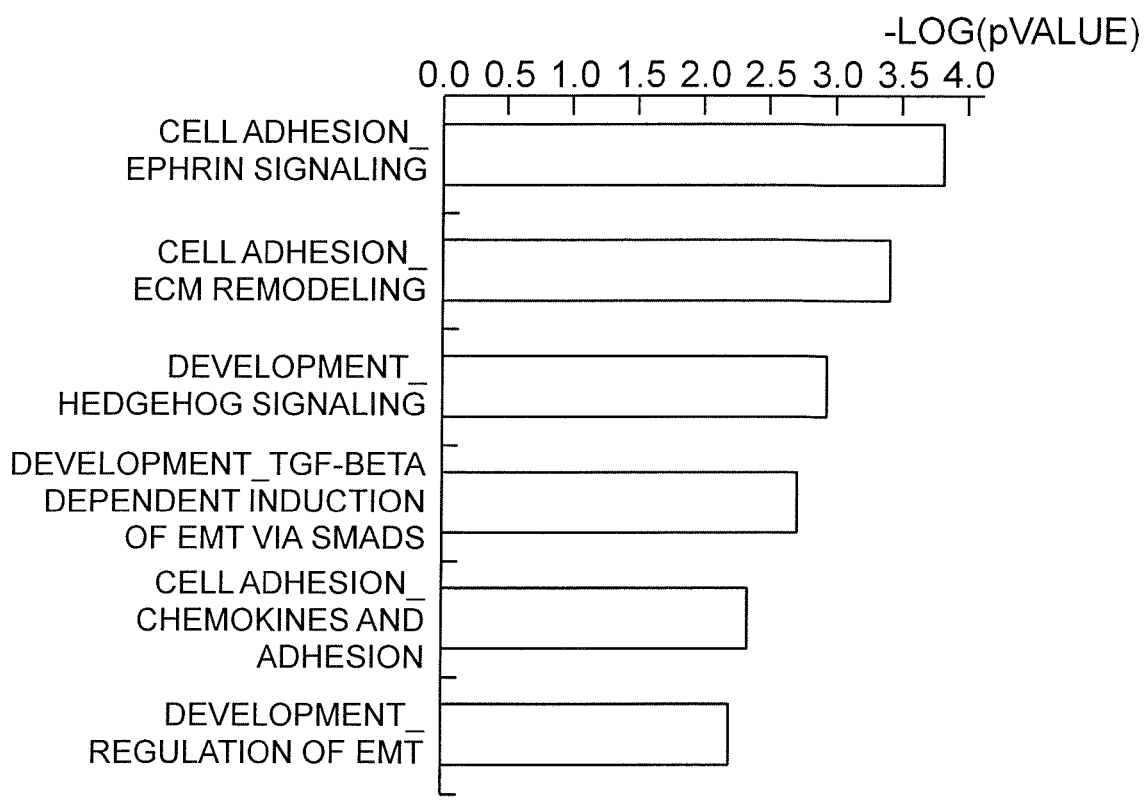

FIG. 3. Gene ontology (GO) analysis of the 669 genes displaying significant changes in expression by microarray profiling of miR-429 transfected HEY cells relative to negative control. The results demonstrated a significant enrichment for genes associated with functions previously associated with EMT and metastasis.

FIGS. 4A-C. Migration, invasion and anchorage-independent growth characteristics of HEY cells transfected with miR-429. (A) HEY cells transfected with miR-429 migrated through pores >2-fold slower and displayed a >5-fold reduction in invasiveness than HEY cells transfected with a negative control microRNA sequence. (B) A representative microscopic image (10×) showing increased migration into a wound line of HEY cells transfected with miR-429 vs HEY cells transfected with a negative control microRNA sequence. (C) The ability of HEY cells transfected with miR-429 to grow in soft agar (anchorage independent grow) was significantly reduced in HEY cells transfected with miR-429 vs. HEY cells transfected with a negative control microRNA sequence.

Figure 5:
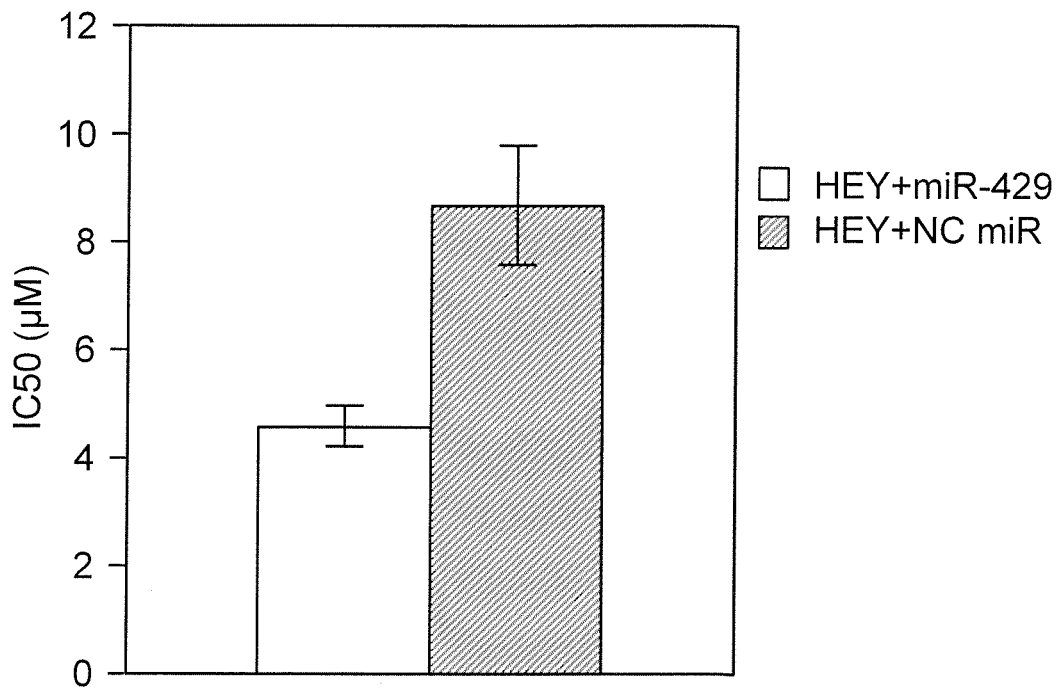

FIG. 5. Effect of miR-429 transfection on responsiveness of Hey cells to cisplatin.

DETAILED DESCRIPTION OF THE INVENTION

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. §1.822 and established usage.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a composition comprises components A, B and C, it is specifically intended that any of A, B or C, or a combination thereof, can be omitted and disclaimed singularly or in any combination. As another example, if the specification states that a particular position in a polynucleotide can be, e.g., C, T or A, it is specifically intended that any of C, T, A, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. Definitions.

As used herein, "a," "an" or "the" can mean one or more than one. For example, "a" miRNA can mean a single species of miRNA or a multiplicity of miRNAs.

Also as used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, *In re Herz*, 537 F.2d 549, 551-52, 190 U.S.P.Q. 461, 463 (CCPA 1976) (emphasis in the original); see also MPEP §2111.03. Thus, the term "consisting essentially of" when used in a claim or the description of this invention is not intended to be interpreted to be equivalent to "comprising."

As used herein the terms "ovarian cancer" and "cancer of the ovary" are used interchangeably. In representative embodiments, these terms refer to "epithelial ovarian cancer" and "epithelial cancer of the ovary" including without limitation the various histological subtypes (e.g., serous, endometrioid, mucinous and/or clear cell) as well as localized (e.g., stage 1) and/or metastatic (e.g., stage 2, 3 and/or 4) cancers. In addition, "ovarian cancer" and "cancer of the ovary" encompass recurrent and/or platinum-resistant or platinum-refractory ovarian cancer. Metastatic disease includes without limitation metastatic lesions to the peritoneal wall, the liver, small intestine, colon, diaphragm and/or omentum and/or malignant ascites.

microRNAs" ("miRNAs") are a class of non-coding RNAs that regulate gene expression and, thereby, biological processes. miRNA are single-stranded RNA molecules that generally range in length from about 20 to about 25 nucleotides in their naturally-occurring form, although shorter and longer miRNA have been identified. miRNA are initially transcribed as a primary miRNA ("pri-miRNA") that is cleaved to form one or more precursor miRNAs ("pre-miRNA"). The pre-miRNA molecule has regions of self-complementarity and forms a stem-loop structure, and is further processed by the enzyme Dicer to produce the "mature" (processed) miRNA. As is known in the art, complete complementary is generally not required between the mature miRNA and the target mRNA sequence; however, it is also known that the "seed" region is generally less tolerant to alterations.

The term "miRNA" includes the primary (pri-miRNA), precursor (pre-miRNA) and/or mature forms of the miRNA. In representative embodiments, the term does not include the pri-miRNA and/or pre-miRNA. The term also includes modified forms (e.g., sequence variants) of the miRNA (e.g., 1 2, 3, 4, 5, or more nucleotides that are substituted, inserted and/or deleted). In representative embodiments, the variant substantially retains at least one biological activity of the wild-type miRNA. The term also includes variants that have been modified to resist degradation within a subject and/or within a cell. The term further includes fragments of a miRNA that substantially retain at least one biological activity of the wild-type miRNA. By "substantially retains" at least one biological activity of the wild-type miRNA means at least about 50%, 60%, 70%, 80%, 90% or more of the biological activity of the wild-type miRNA. The one or more biological activities can include any relevant activity, including without limitation, binding activity (e.g., to a target mRNA), reduction or inhibition of EMT, induction of MET, prevention of metastasis, treating ovarian cancer, increasing the sensitivity of a cancer cell to a cytotoxic agent, and the like.

The term "miRNA polynucleotide," as used herein, refers to a polynucleotide that is the mature miRNA, the pre-miRNA, pri-miRNA and any other polynucleotide sequence that can be processed in a cell to produce the mature miRNA. In representative embodiments, the term "miRNA polynucleotide" does not encompass the pri-miRNA and/or pre-miRNA.

The term "nucleic acid," "polynucleotide" or "nucleotide sequence" can be used interchangeably herein unless the context indicates otherwise. These terms encompass both RNA and DNA, including cDNA, genomic DNA, synthetic (e.g., chemically synthesized) RNA and DNA, and chimeras of RNA and DNA. The nucleic acid, polynucleotide or nucleotide sequence may be double-stranded or single-stranded, and further may be synthesized using nucleotide analogs or derivatives (e.g., inosine or phosphorothioate nucleotides). Such nucleotides can be used, for example, to prepare nucleic acids, polynucleotides and nucleotide sequences that have altered base-pairing abilities or increased resistance to nucleases. The present invention further provides a nucleic acid, polynucleotide or nucleotide sequence that is the complement (which can be either a full complement or a partial complement) of a nucleic acid, polynucleotide or nucleotide sequence of the invention (e.g., encodes a nucleic acid, polynucleotide or nucleotide sequence comprising a miRNA of the invention).

Optionally, the nucleic acid or polynucleotide of the invention is "isolated." An "isolated" nucleic acid or polynucleotide is a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated nucleic acid or polynucleotide includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid or polypeptide encoding an additional polypeptide or peptide sequence. In representative embodiments, the "isolated" nucleic acid or polypeptide that is substantially free of cellular material, viral material, and/or culture medium (when produced by recombinant DNA techniques), or chemical precursors or other chemicals (when chemically synthesized). Optionally, In representative embodiments, the isolated nucleic acid or polynucleotide is at least about 10%, 20%, 30%, 40%, 50%, 60%, 70%, 80%, 90%, 95% or more pure.

The term "fragment," as applied to a nucleic acid or polynucleotide, will be understood to mean a nucleotide sequence of reduced length relative to a reference nucleotide sequence and comprising, consisting essentially of, and/or consisting of a nucleotide sequence of contiguous nucleotides identical or almost identical (e.g., 90%, 92%, 95%, 98%, 99% identical) to the reference nucleotide sequence. Such a fragment according to the invention may be, where appropriate, included in a larger polynucleotide of which it is a constituent. In some embodiments, such fragments can comprise, consist essentially of, and/or consist of oligonucleotides having a length of at least about 8, 10, 12, 15, 16, 17, 18, 19, 20, 25, 30, 35, 40, 45, 50, 75, 100, 125, 150, 200, or more. In representative embodiments, the fragment substantially retains (e.g., at least about 50%, 60%, 70%, 80%, 90% or more) at least one activity of the full-length nucleic acid or polynucleotide.

A "vector" is any nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in vivo, i.e., capable of replication under its own control. The term "vector" includes both viral and nonviral (e.g., plasmid) nucleic acid molecules for introducing a nucleic acid into a cell in vitro, ex vivo, and/or in vivo, and is optionally an expression vector. A large number of vectors known in the art may be used to manipulate, deliver and express polynucleotides. Vectors may be engineered to contain sequences encoding selectable markers that provide for the selection of cells that contain the vector and/or have integrated some or all of the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences transgenes), e.g., two, three, four, five or more heterologous nucleotide sequences.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, and/or adenovirus vectors. Non-viral vectors include, but are not limited to, plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

By the term "express" or "expression" of a polynucleotide sequence, it is meant that the sequence is transcribed, and optionally, translated. As is understood in the art, miRNA are non-translated RNA sequences.

"Effective amount" as used herein refers to an amount of a miRNA, vector, nucleic acid, polynucleotide, composition or formulation (e.g., liposome or nanoparticle) of the invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation.

By the term "treat," "treating" or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay in the progression of the disease or disorder. In representative embodiments, the term "treat,", "treating" or "treatment of" (and grammatical variations thereof) refer to a reduction in the severity of cancer, a delay in the progression of the cancer, a delay in recurrence of the cancer, a reduction in metastatic lesions, an increased progression free survival period and/or an increased overall survival.

A "treatment effective" amount as used herein is an amount that is sufficient to treat (as defined herein) the subject. Those skilled in the art will appreciate that the therapeutic effects need not be complete or curative, as long as some benefit is provided to the subject.

The term "prevent," "preventing" or "prevention of" (and grammatical variations thereof) refer to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. In representative embodiments, the term "prevent,", "preventing" or "prevention of" (and grammatical variations thereof) refer to prevention and/or delay of the onset and/or progression of the cancer, a delay and/or reduction in recurrence of the cancer and/or a reduction in the onset and/or extent of metastasis. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention. "Prevention" of metastasis can refer to a subject that has or has had localized disease in which the onset of metastasis is prevented and/or to a subject that has or has had metastatic disease in which further metastasis is prevented.

A "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

As used herein, the terms "reduce," "reduces," "reduction" and similar terms mean a decrease of at least about 25%, 35%, 50%, 75%, 80%, 85%, 90%, 95%, 97% or more. In particular embodiments, the reduction results in no or essentially no (i.e., an insignificant amount, e.g., less than about 10% or even 5%) detectable activity or cancer.

As used herein, the terms "increase," "increases," "increasing" and similar terms indicate an elevation of at least about 25%, 50%, 75%, 100%, 150%, 200%, 300%, 400%, 500% or more.

The term "epithelial phenotype" is understood in the art, and can be identified by morphological, molecular and/or functional characteristics. For example, epithelial cells generally have a rounded or cobblestone appearance, express the epithelial marker E-cadherin, are rapidly dividing and/or have relatively low levels of motility, invasiveness and/or anchorage-independent growth as compared with mesenchymal cells.

The term "mesenchymal phenotype" is understood in the art, and can be identified by morphological, molecular and/or functional characteristics. For example, mesenchymal cells generally have an elongated or spindle-shaped appearance, express the mesenchymal markers vimentin, fibronectin and N-cadherin, divide slowly or are non-dividing and/or have relatively high levels of motility, invasiveness and/or anchorage-independent growth as compared with epithelial cells.

The term "epithelial-to-mesenchymal transition" ("EMT") is known in the art and refers to a process whereby epithelial cancer cells take on a mesenchymal phenotype, which is believed to be associated with metastasis. In addition, while not wishing to be limited by any theory, these mesenchymal cells generally display reduced adhesiveness, increased motility and invasiveness and are relatively resistant to chemotherapeutic agents and/or radiation (e.g., treatments that target rapidly dividing cells).

The term "mesenchymal-to-epithelial transition" ("MET") is also known in the art and refers to the reprogramming of cells that have undergone EMT to regain one or more epithelial characteristics (e.g., as described above). For example, such cells typically exhibit reduced motility and/or invasiveness and/or are rapidly dividing, and may thereby regain sensitivity to cytotoxic agents.

A "subject" of the invention includes any animal susceptible to ovarian cancer. Such a subject is generally a mammalian subject (e.g., a laboratory animal such as a rat, mouse, guinea pig, rabbit, primates, etc.), a farm or commercial animal (e.g., a cow, horse, goat, donkey, sheep, etc.), or a domestic animal (e.g., cat, dog, ferret, etc.). In particular embodiments, the subject is a primate subject, a non-human primate subject (e.g., a chimpanzee, baboon, monkey, gorilla, etc.) or a human. Subjects of the invention can be a subject known or believed to be at risk of ovarian cancer. In representative embodiments, the subject is a subject that has or has had ovarian cancer (e.g., is in remission).

Subjects include females of any age that have, have had and/or or are at risk for ovarian cancer, including juvenile, mature and geriatric subjects. With respect to human subjects, in representative embodiments, the subject is generally an adult or geriatric subject, although teen and pre-teen girls have been diagnosed with ovarian cancer.

A "subject in need" of the methods of the invention can be any subject that currently has and/or has had in the past, ovarian cancer and/or is a subject known to be, or suspected of being, at risk of ovarian cancer. In embodiments of the invention, a "subject in need thereof" is a subject that has or has had (e.g., is in remission) ovarian cancer. Optionally, the subject has, or appears to have, localized disease and the method is practiced to prevent recurrence and/or metastasis. In other embodiments, the subject has, or has had, metastatic ovarian cancer and the method is practiced to prevent recurrence and/or further metastatic disease and/or to extend progression free survival and/or overall survival. In various embodiments, the subject is resistant or refractory to one or more cytotoxic agents (e.g., a platinum chemotherapeutic agent and/or a taxane) and the invention is practiced to reduce the level of resistance or refractoriness to the cytotoxic agent(s) (e.g., to sensitize the cancer the cytotoxic agent(s)). In further embodiments, the subject has recurrent ovarian cancer, and the invention is practiced to treat the disease, to extend progression free survival and/or overall survival.

In embodiments of the invention, the subject has localized (e.g., stage 1) ovarian cancer. In embodiments of the invention, the subject has metastatic ovarian cancer (e.g., stage 2, 3 and/or 4).

In embodiments of the invention, the subject is in remission from ovarian cancer.

In embodiments of the invention, the subject has or has had recurrent ovarian cancer.

In embodiments of the invention, the subject's cancer is resistant or refractory to a cytotoxic therapy, e.g., chemotherapy and/or radiation therapy. In embodiments of the invention, the subject is resistant or refractory to a platinum-based chemotherapy agent (e.g., carboplatin, cisplatin and/or oxaliplatin), a taxane (e.g., taxol, paclitaxel albumin-bound particles [ABRAXANE®], a nucleotide analog (e.g., gemcitabine), a topoisomerase I inhibitor (e.g., a camptothecin analogue such as irinotecan or topotecan), a topoisomerase II inhibitor (e.g., etoposide [VP-16]) and/or DNA intercalators such as doxorubicin (e.g., ADRIAMYCIN®, DOXIL®).

A "cytotoxic" therapy or agent is one that induces cell death (as opposed to a cytostatic therapy) and includes chemotherapy and/or radiation therapy. Cytotoxic chemotherapy agents include without limitation a platinum-based chemotherapy agent (e.g., carboplatin, cisplatin and/or oxaliplatin), a taxane (e.g., taxol, paclitaxel albumin-bound particles [ABRAXANE®], a nucleotide analog (e.g., gemcitabine), a topoisomerase I inhibitor (e.g., a camptothecin analogue such as irinotecan or topotecan), a topoisomerase II inhibitor (e.g., etoposide [VP-16]) and/or a DNA intercalator such as doxorubicin (e.g., ADRIAMYCIN®, DOXIL®). Cytotoxic therapies and agents also include DNA damaging agents, e.g., an agent that damages DNA and, consequently, induces apoptosis. Examples of DNA damaging agents include, but are not limited to, alkylating agents (e.g., cisplatin, carboplatin, ifosfamide, chlorambucil, busulfan and thiotepa), doxorubicin, etoposide, mitomycin C, cisplatin, etoposide and radiation therapy. Particular immune therapies (e.g., monoclonal antibodies) may also be cytotoxic. Cytotoxic therapies are generally more effective on cells with an epithelial phenotype (e.g., rapidly dividing) as opposed to cells with mesenchymal phenotype (e.g., slowly dividing or non-dividing). Without wishing to be limited to any theory of the invention, in representative embodiments, the present invention induces mesenchymal-to-epithelial transition (MET) thereby sensitizing cancer cells to a cytotoxic agent.

By "sensitizing" a cancer or a cancer cell (e.g., a cancer stem cell and/or a cancer cell with a mesenchymal phenotype) to a cytotoxic therapy or "increasing the sensitivity" of a cancer or cancer cell to a cytotoxic therapy it is meant that lower dosages of the cytotoxic agent are effective to treat the cancer or kill the cancer cell and/or the cancer or cancer cell is more responsive to the same dosage of the cytotoxic agent as compared with the response in the absence of the methods and compositions of the invention. In representative embodiments, the cancer is resistant or refractory to the cytotoxic agent, and by "sensitizing" the cancer, the level of resistance or refractoriness to the cytotoxic agent is reduced.

By "resistant" or "refractory" it is meant that the cancer or cancer cell is poorly responsive or essentially non-responsive to the therapy (or even progresses while the subject is receiving the therapy), respectively. For example, platinum-resistant ovarian cancer is sometimes defined as cancer in which a remission of six months or less is achieved following treatment with a platinum-based chemotherapy agent, and a platinum refractory cancer is one in which no remission is achieved or the cancer progresses during treatment with a platinum-based agent.

By "delivering" (and grammatical variants) a miRNA to a cell or subject it is meant that the miRNA is provided to the cell or subject directly or indirectly, e.g., the miRNA itself is administered to the cell or subject, a polynucleotide comprising or consisting essentially of the miRNA is administered to the cell or subject, or a polynucleotide encoding the miRNA (for example, a polynucleotide comprising, consisting essentially of, or consisting of the complement of the miRNA) is administered to the cell or subject. Further, a vector, liposome or nanoparticle (each as described in more detail herein) comprising or encoding any of the foregoing can be administered to the cell or subject.

By "administered" or "administration" (and other grammatical variants) is meant that the indicated miRNA, polynucleotide, vector, liposome, nanoparticle, and the like is directly administered to the subject. For example, if a mature miRNA is "administered" or "directly administered" to the subject, it is intended that the mature miRNA itself is given or administered to the subject, rather than a precursor molecule that is processed to provide the mature miRNA or a polynucleotide that encodes the mature miRNA. "Administration" or "direct administration" encompasses the possibility that the indicated miRNA, polynucleotide, vector, etc. is administered by a nanoparticle, a liposome, or other delivery system.

miR-200 Family Members.

The term "miR-200 family member" refers to a miRNA in the miR-200 family, which currently includes miR-200a, miR-200b, miR-200c, miR-141 and miR-429. These miR-NAs are encoded in two clusters in the human genome: miR-200a, miR-200b and miR-429 are generated as a polycistronic transcript from human chromosome 1, and miR-141 and miR-200c as a single transcript from chromosome 12. Unless indicated otherwise, the term also includes the primary (pri-miRNA), precursor (pre-miRNA) and/or mature forms of these miRNAs. In representative embodiments, the term does not include the pri-miRNA and/or pre-miRNA. The term also includes modified forms (e.g., sequence variants) of members of the miR-200 family (e.g., 1 2, 3, 4, 5, or more nucleotides that are substituted, inserted and/or deleted). In representative embodiments, the variant substantially retains at least one biological activity of the wild-type miRNA. The term also includes variants that have been modified to resist degradation within a subject and/or within a cell. The term further includes fragments of a miR-200 family member that substantially retain at least one biological activity of the wild-type mi-RNA. By "substantially retains" at least one biological activity of the wild-type miRNA means at least about 50%, 60%, 70%, 80%, 90% or more of the biological activity of the wild-type miRNA. The one or more biological activities can include any relevant activity, including without limitation, binding activity (e.g., to a target mRNA), reduction or inhibition of EMT, induction of MET, prevention of metastasis, treating ovarian cancer, increasing the sensitivity of a cancer cell to a cytotoxic agent, and the like.

Unless indicated otherwise, the miR-200 family member can be from any animal species (including sequence variants, fragments, primary, precursor and mature forms as discussed in the preceding paragraph). In representative embodiments, the miR-200 family member is a mammalian miR-200 family member, optionally a human miR-200 family member (which can be designated by the prefix "hsa"), which would encompass modified forms and fragments thereof as discussed above. The nucleotide sequences of miR-200 family members are known in the art (e.g., in the miRBase database or NCBI database). For example, the nucleotide sequence of the pre-mRNA can be found as follows: pre-miR-141 (NCBI Accession No. NR_029682), pre-miR-200a (NCBI Accession No. NR_029834), pre-miR-200b (NCBI Accession No. NR_029639), pre-miR-200c (NCBI Accession No. NR_029779), and pre-miR-429 (NCBI Accession No. NR_029957). See also, the mature and seed sequences for the miR-200 family members in Uhlmann et al., Oncogene 2010; 29, 4297-4306).

The precursor, mature and seed sequences of the human miR-200 (hsa-miR-200) family members is shown below in Table 1.

3, 4, 5 or more nucleotides that are substituted, inserted and/or deleted outside of the seed region, but the seed region is not modified.

Thus, for example, with particular respect to miR-429, a modified form thereof might contain 1, 2, 3, 4, 5 or more of the following nucleotides changes, with no modifications in the seed sequence:

The "U" at position 1 of miR-429 can be replaced by an A, C and/or G and/or can be deleted.

The "U" at position 9 of miR-429 can be replaced by an A, C and/or G and/or can be deleted.

The "C" at position 10 of miR-429 can be replaced by an A, G and/or U and/or can be deleted.

The "U" at position 11 of miR-429 can be replaced by an A, C and/or G and/or can be deleted.

The "G" at position 12 of miR-429 can be replaced by an A, C and/or U and/or can be deleted.

The "G" at position 13 of miR-429 can be replaced by an A, C and/or U and/or can be deleted.

The "U" at position 14 of miR-429 can be replaced by an A, C and/or G and/or can be deleted.

The "A" at position 15 of miR-429 can be replaced by a C, G and/or U and/or can be deleted.

| hsa-miR-200 Family Member | Precursor miRNA | Mature miRNA (with seed region underlined) |
|---|---|---|
| miR-200b | CCAGCUCGGGCAGCCGUGGCC AUCUUACUGGGCAGCAUUGGA UGGAGUCAGGUCUCUAAUACU GCCUGGUAAUGAUGACGGCGG AGCCCUGCACG (SEQ ID NO: 1) | UAAUACUGCCUGGUAAUGAUGA (SEQ ID NO: 2) |
| miR-200c | CCCUCGUCUUACCCAGCAGUG UUUGGGUGCGGUUGGGAGUCU CUAAUACUGCCGGGUAAUGAU GGAGG (SEQ ID NO: 3) | UAAUACUGCCGGGUAAUGAUGGA (SEQ ID NO: 4) |
| miR-429 | CGCCGGCCGAUGGGCGUCUUA CCAGACAUGGUUAGACCUGGC CCUCUGUCUAAUACUGUCUGG UAAAACCGUCCAUCCGCUGC (SEQ ID NO: 5) | UAAUACUGUCUGGUAAAACCGU (SEQ ID NO: 6) |
| miR-141 | CGGCCGGCCCUGGGUCCAUCU UCCAGUACAGUGUUGGAUGGU CUAAUUGUGAAGCUCCUAACA CUGUCUGGUAAAGAUGGCUCC CGGGUGGGUUC (SEQ ID NO: 7) | UAACACUGUCUGGUAAAGAUGG (SEQ ID NO: 8) |
| miR-200a | CCGGGCCCCUGUGAGCAUCUU ACCGGACAGUGCUGGAUUUCC CAGCUUGACUCUAACACUGUC UGGUAACGAUGUUCAAAGGUG ACCCGC (SEQ ID NO: 9) | UAACACUGUCUGGUAACGAUGU (SEQ ID NO: 10) |

The miR-200 family members can also be classified based on the "seed" sequence. miR-200b, miR-200c and miR-429 share the seed sequence AAUACUG, whereas miR-141 and miR-200a share the seed sequence AACACUG. In representative embodiments, a modified miR-200b, miR200c or miR-429 of the invention (including fragments) comprises the seed sequence AAUACUG. In representative embodiments, a modified miR-141 or miR-200a of the invention (including fragments) comprises the seed sequence AACACUG. According to these embodiments, the miRNA can have 1, 2, The "A" at position 16 of miR-429 can be replaced by a C, G and/or U and/or can be deleted.

The "A" at position 17 of miR-429 can be replaced by a C, G and/or U and/or can be deleted.

The "A" at position 18 of miR-429 can be replaced by a C, G and/or U and/or can be deleted.

The "C" at position 19 of miR-429 can be replaced by an A, G and/or U and/or can be deleted.

The "C" at position 20 of miR-429 can be replaced by an A, G and/or U and/or can be deleted.

The "G" at position 21 of miR-429 can be replaced by an A, C and/or U and/or can be deleted.

The "U" at position 22 of miR-429 can be replaced by an A, C and/or G and/or can be deleted.

In embodiments of the invention, the miR-200 family member comprises, consists essentially of, or consists of the pre-miR-141, pre-miR-200a, pre-miR-200b, pre-miR-200c and/or pre-miR-429.

In embodiments of the invention, the miR-200 family member comprises, consists essentially of, or consists of the human pre-miR-141 (SEQ ID NO:7), pre-miR-200a (SEQ ID NO:9), pre-miR-200b (SEQ ID NO:1), pre-miR-200c (SEQ ID NO:3) and/or pre-miR-429 (SEQ ID NO:5).

In embodiments of the invention, the miR-200 family member comprises, consists essentially of, or consists of the mature miR-141, miR-200a, miR-200b, miR-200c and/or miR-429.

In embodiments of the invention, the miR-200 family member comprises, consists essentially of, or consists of the mature human miR-141 (SEQ ID NO:8), miR-200a (SEQ ID NO:10), miR-200b (SEQ ID NO:2), miR-200c (SEQ ID NO:4) and/or miR-429 (SEQ ID NO:6).

A microRNA can be constructed using chemical synthesis and enzymatic ligation reactions by procedures known in the art. For example, a microRNA can be chemically synthesized using naturally occurring nucleotides or various modified nucleotides designed to increase the biological stability of the molecules or to increase the physical stability of the duplex formed between the microRNA and target nucleotide sequences, e.g., phosphorothioate derivatives and acridine substituted nucleotides can be used. Examples of modified nucleotides which can be used to generate the microRNA include, but are not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomet-hyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopenten-yladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

The microRNA can further include nucleotide sequences wherein at least one, or all, of the internucleotide bridging phosphate residues are modified phosphates, such as methyl phosphonates, methyl phosphonothioates, phosphoromorpholidates, phosphoropiperazidates and phosphoramidates. For example, every other one of the internucleotide bridging phosphate residues can be modified as described. In another non-limiting example, the microRNA is a nucleotide sequence in which one, or all, of the nucleotides contain a 2' lower alkyl moiety (e.g., $C_1$-$C_4$, linear or branched, saturated or unsaturated alkyl, such as methyl, ethyl, ethenyl, propyl, 1-propenyl, 2-propenyl, and isopropyl). For example, every other one of the nucleotides can be modified as described. See also, Furdon et al., *Nucleic Acids Res.* 17:9193 (1989); Agrawal et al., *Proc. Natl. Acad. Sci. USA* 87:1401 (1990); Baker et al., *Nucleic Acids Res.* 18:3537 (1990); Sproat et al., *Nucleic Acids Res.* 17:3373 (1989); Walder and Walder, *Proc. Natl. Acad. Sci. USA* 85:5011 (1988)).

Alternatively, the microRNA can be produced using an expression vector into which a nucleic acid encoding the microRNA has been cloned.

The microRNAs of the invention can be delivered directly into a cell by any method known in the art, e.g., by transfection, microinjection and/or a nanoparticle delivery system. In representative embodiments, the pre-miRNA, the pre-miRNA and/or the mature miRNA can be administered to a cell. Alternately, a polynucleotide comprising or consisting essentially of the pri-miRNA, pre-miRNA and/or mature miRNA can be administered to the subject, which can optionally be processed to provide the mature miRNA. In other embodiments, the miRNA can be delivered to a subject in the form of a polynucleotide (e.g., a delivery vector) that encodes and expresses a mRNA within the cells of the subject.

Those skilled in the art will appreciate that the polynucleotides encoding the miRNAs of the invention will typically be associated with appropriate expression control sequences, e.g., transcription/translation control signals and polyadenylation signals.

In representative embodiments, the isolated polynucleotide encoding the miRNA is incorporated into an expression vector. Expression vectors compatible with various host cells are well known in the art and contain suitable elements for transcription and translation of nucleic acids. Typically, an expression vector contains an "expression cassette," which includes, in the 5' to 3' direction, a promoter, a coding sequence encoding a miRNA operatively associated with the promoter, and, optionally, a termination sequence including a stop signal for RNA polymerase and a polyadenylation signal for polyadenylase.

It will further be appreciated that a variety of promoter/enhancer elements can be used depending on the level and tissue-specific expression desired. The promoter can be constitutive or inducible, depending on the pattern of expression desired. The promoter can be native or foreign and can be a natural or a synthetic sequence. By foreign, it is intended that the transcriptional initiation region is not found in the wild-type host into which the transcriptional initiation region is introduced. The promoter is chosen so that it will function in the target cell(s) of interest.

To illustrate, the coding sequence can be operatively associated with an animal or mammalian promoter, including without limitation a cytomegalovirus (CMV) major immediate-early promoter, an albumin promoter, an Elongation Factor 1-α (EF1-α) promoter, a PγK promoter, a MFG promoter, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the herpes simplex virus (HSV) thymidine kinase (TK) promoter, baculovirus IE1 promoter, phosphoglycerate kinase (PGK) promoter, ubiquitin (Ubc) promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), and pathogenesis and/or disease-related promoters.

Other non-limiting examples of promoters include, but are not limited to, CYC1, HIS3, GAL1, GAL4, GAL10, ADH1, PGK, PHO5, GAPDH, ADC1, TRP1, URA3, LEU2, ENO, TPI, and alkaline phosphatase promoters (useful for expression in *Saccharomyces*); AOX1 promoter (useful for expression in *Pichia*); and the β-lactamase, lac, ara, tet, trp, $IP_L$, $IP_R$, T7, tac, and trc promoters (useful for expression in *Escherichia coli*).

Inducible promoter/enhancer elements include hormone-inducible and metal-inducible elements, and other promoters regulated by exogenously supplied compounds, including without limitation, the zinc-inducible metallothionein (MT) promoter; the dexamethasone (Dex)-inducible mouse mammary tumor virus (MMTV) promoter; the T7 polymerase promoter system (see WO 98/10088); the ecdysone insect promoter (No et al., *Proc. Natl. Acad. Sci. USA* 93:3346 (1996)); the tetracycline-repressible system (Gossen et al., *Proc. Natl. Acad. Sci. USA* 89:5547 (1992)); the tetracycline-inducible system (Gossen et al., *Science* 268:1766 (1995); see also Harvey et al., *Curr. Opin. Chem. Biol.* 2:512 (1998)); the RU486-inducible system (Wang et al., *Nat. Biotech.* 15:239 (1997); Wang et al., *Gene Ther.*, 4:432 (1997)); and the rapamycin-inducible system (Magari et al., *J. Clin. Invest.* 100: 2865 (1997)).

Other tissue-specific promoters or regulatory promoters include, but are not limited to, promoters that typically confer tissue-specific or preferred expression in ovarian cells and tissue, for example, the OSP-1 (Ovarian Specific Promoter 1) promoter, the ovary-specific PII promoter of the aromatase gene, and the 5' upstream regulatory sequences of the mouse misiir (Müllerian inhibitory substance type II receptor) gene.

Enhancers that may be used in embodiments of the invention include but are not limited to: an SV40 enhancer, a cytomegalovirus (CMV) enhancer, an elongation factor I (EF1) enhancer, yeast enhancers, viral gene enhancers, and the like.

Termination control regions, i.e., terminator or polyadenylation sequences, may be derived from various genes native to the preferred hosts. In some embodiments of the invention, the termination control region may comprise or be derived from a synthetic sequence, a synthetic polyadenylation signal, an SV40 late polyadenylation signal, an SV40 polyadenylation signal, a bovine growth hormone (BGH) polyadenylation signal, viral terminator sequences, or the like.

It will be apparent to those skilled in the art that any suitable vector can be used to deliver the polynucleotide to a cell or subject. The vector can be delivered to cells in vivo. In other embodiments, the vector can be delivered to cells ex vivo, and then cells containing the vector are delivered to the subject. The choice of delivery vector can be made based on a number of factors known in the art, including age and species of the target host, in vitro versus in vivo delivery, level and persistence of expression desired, intended purpose (e.g., for therapy or research), the target cell or organ, route of delivery, size of the isolated polynucleotide, safety concerns, and the like.

Suitable vectors include, but are not limited to, plasmid vectors, viral vectors (e.g., retrovirus, alphavirus; vaccinia virus; adenovirus, adeno-associated virus and other parvoviruses, lentivirus, poxvirus, or herpes simplex virus), lipid vectors, poly-lysine vectors, synthetic polyamino polymer vectors, and the like.

Any viral vector that is known in the art can be used in the present invention. Protocols for producing recombinant viral vectors and for using viral vectors for nucleic acid delivery can be found in Ausubel et al., Current Protocols in Molecular Biology (Green Publishing Associates, Inc. and John Wiley & Sons, Inc., New York) and other standard laboratory manuals (e.g., Vectors for Gene Therapy. In: *Current Protocols in Human Genetics*. John Wiley and Sons, Inc.: 1997).

Non-viral transfer methods can also be employed. Many non-viral methods of nucleic acid transfer rely on normal mechanisms used by mammalian cells for the uptake and intracellular transport of macromolecules. In particular embodiments, non-viral nucleic acid delivery systems rely on endocytic pathways for the uptake of the nucleic acid molecule by the targeted cell. Exemplary nucleic acid delivery systems of this type include liposomal derived systems, poly-lysine conjugates, and artificial viral envelopes.

In particular embodiments, plasmid vectors are used in the practice of the present invention. Expression can extend over many months, although the number of positive cells is typically low (Wolff et al., *Science* 247:247 (1989)). Cationic lipids have been demonstrated to aid in introduction of nucleic acids into some cells in culture (Felgner and Ringold, *Nature* 337:387 (1989)). One advantage of plasmid DNA is that it can be introduced into non-replicating cells.

Expression vectors can be designed for expression of miRNAs in prokaryotic or eukaryotic cells. For example, miRNAs can be expressed in bacterial cells such as *E. coli*, insect cells (e.g., the baculovirus expression system), yeast cells, plant cells or mammalian cells. Some suitable host cells are discussed further in Goeddel, *Gene Expression Technology: Methods in Enzymology* 185, Academic Press, San Diego, Calif. (1990). Examples of bacterial vectors include, but are not limited to, pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, and pRIT5 (Pharmacia). Examples of vectors for expression in the yeast *S. cerevisiae* include pYepSecI (Baldari et al., *EMBO J.* 6:229 (1987)), pMFa (Kurjan and Herskowitz, *Cell* 30:933 (1982)), pJRY88 (Schultz et al., *Gene* 54:113 (1987)), and pYES2 (Invitrogen Corporation, San Diego, Calif.). Non-limiting examples of baculovirus vectors available for expression of nucleic acids to produce proteins in cultured insect cells (e.g., Sf 9 cells) include the pAc series (Smith et al., *Mol. Cell. Biol.* 3:2156 (1983)) and the pVL series (Lucklow and Summers *Virology* 170:31 (1989)).

Examples of mammalian expression vectors include pWL-NEO, pSV2CAT, pOG44, pXT1, pSG (Stratagene) pSVK3, PBPV, pMSG, PSVL (Pharmacia), pCDM8 (Seed, *Nature* 329:840 (1987)) and pMT2PC (Kaufman et al., *EMBO J.* 6:187 (1987)). When used in mammalian cells, the expression vector's control functions are often provided by viral regulatory elements. For example, commonly used promoters are derived from polyoma, adenovirus 2, cytomegalovirus and Simian Virus 40.

In addition to the regulatory control sequences discussed above, the recombinant expression vector can contain additional nucleotide sequences. For example, the recombinant expression vector can encode a selectable marker gene to identify host cells that have incorporated the vector.

Delivery Methods.

The present invention also encompasses methods of delivering or administering one or more miR-200 family members to a cell (in vitro, ex vivo and in vivo) or to a subject. The one or more miR-200 family members can be delivered or administered to the cell or subject for any reason, e.g., for research purposes to study the mechanism of action of the miRNA(s), to modulate cell behavior in vitro or in vivo and/or for therapeutic purposes.

In representative embodiments, one or more miR-200 family members are delivered or administered to a cell or to a subject to reduce EMT in the cell or subject. Accordingly, in exemplary embodiments, the invention provides a method of reducing EMT in an ovarian cancer cell (e.g., a cell with an epithelial phenotype), the method comprises delivering or administering one or more miR-200 family members to a cell in an amount effective to reduce EMT in the cell. In other embodiments, the invention provides a method of reducing EMT in an ovarian cancer, the method comprising delivering or administering one or more miR-200 family members to a mammalian subject in need thereof in an amount effective to reduce EMT in the ovarian cancer.

The invention also contemplates a method of inducing MET in an ovarian cancer cell, the method comprising delivering or administering one or more miR-200 family members to an ovarian cancer cell (e.g., a cell with a mesenchymal phenotype and/or an ovarian cancer stem cell) in an amount effective to induce MET in the cell. The invention further provides a method of inducing MET in an ovarian cancer, the method comprising delivering or administering one or more miR-200 family members to a mammalian subject in need thereof in an amount effective to induce MET in the ovarian cancer.

The invention further provides a method of treating an ovarian cancer, the method comprising delivering or administering one or more miR-200 family members to a mammalian subject in need thereof in an amount effective to treat the ovarian cancer.

As another aspect, the invention provides a method of preventing metastasis of an ovarian cancer, the method comprising delivering or administering one or more miR-200 family members to a mammalian subject in need thereof in an amount effective to prevent metastasis.

The invention further provides a method of sensitizing an ovarian cancer to a cytotoxic therapy (e.g., increasing the sensitivity to a cytotoxic therapy), the method comprising delivering or administering one or more miR-200 family members to a mammalian subject in need thereof in an amount effective to sensitize the ovarian cancer to the cytotoxic therapy. Also provided is a method of sensitizing an ovarian cancer cell (e.g., a metastatic cell, an ovarian cancer stem cell) to a cytotoxic therapy, the method comprising delivering or administering one or more miR-200 family members to an ovarian cancer cell in an amount effective to sensitize the ovarian cancer cell to the cytotoxic therapy. While not wishing to be bound by any theory, delivering one or more miR-200 family members to the subject or cancer cell can be practiced to reduce and/or prevent the level of resistance or refractoriness to a cytotoxic therapy.

According to representative embodiments, any of the inventive methods of delivering or administering to a subject of can further comprise detecting a level of one or more miR-200 family members in ovarian cancer tissue from the subject prior to administering the one or more miR-200 family members to the subject. The level of the miRNAs can be detected in a tissue sample ex vivo or in situ. For example, a tumor sample or ascites fluid can be removed from the subject and the level of the one or more miR-200 family members evaluated. Optionally, the level in the tumor sample or ascites can be compared with a reference value (e.g., based on the levels of the one or more miR-200 family member in ovarian epithelial cells), and if the level is below the reference value, the one or more miR-200 family members are delivered to the subject.

The methods of the invention can further comprise detecting a level of cells having a mesenchymal phenotype in ovarian cancer tissue from the subject prior to administering the one or more miR-200 family members to the subject. The level of mesenchymal cells can be evaluated ex vivo (e.g., in a tumor sample or ascites) or in situ. According to this embodiment, if the presence of mesenchymal cells are detected, the one or more miRNAs are delivered to the subject. Methods of detecting the level of mesenchymal cells can comprise methods of detecting the presence or absence of mesenchymal cells as well as quantitative and semi-quantitative methods.

According to any of the inventive methods, a cytotoxic therapy can be administered prior to, concurrently with and/or after administration of the one or more miR-200 family members to a subject. By "concurrently" it is meant that the two treatments are sufficiently close in time to have a combined effect. In embodiments of the invention, the one or more miR-200 family members are delivered to the subject concurrently with and/or within about 3 hours to about 24, 48, 72, 96, 120, 144 or 168 hours prior to administration of a cytotoxic therapy, within about 6 hours to about 24, 48, 72, 96, 120, 144 or 168 hours prior to administration of a cytotoxic treatment, within about 12 hours to about 24, 48, 72, 96, 120, 144 or 168 hours prior to administration of a cytotoxic therapy, within about 24 hours to about 48, 72, 96, 120, 144 or 168 hours prior to administration of a cytotoxic therapy, within about 36 hours to about 72, 96, 120, 144 or 168 hours prior to administration of a cytotoxic therapy, within about 48 hours to about 72, 96, 120, 144 or 168 hours prior to administration of a cytotoxic therapy, or within about 72 hours to about 96, 120, 144 or 168 hours prior to administration of a cytotoxic therapy.

In particular embodiments of the invention, more than one administration (e.g., two, three, four, or more administrations) can be employed over a variety of time intervals (e.g., hourly, daily, weekly, monthly, etc.) to achieve therapeutic effects.

miR-200 family members are described in detail herein. In embodiments of the invention, the one or more miR-200 family members comprise or consist of miR-141, miR-200a, miR-200b, miR-200c, miR-205 and/or miR-429, in any combination.

In embodiments of the invention, the one or more miR-200 family members comprise or consist of miR-200a, miR-200b and/or miR-429, in any combination. For example, the one or more miR-200 family members can comprise or consist of (i) miR-200a and miR-429; or (ii) miR-200b and miR-429.

In embodiments of the invention, the one or more miR-200 family members comprise or consist of miR-141 and/or miR-200c.

In embodiments of the invention, the one or more miR-200 family members comprise or consist of miR200b, miR200-c and/or miR-429. For example, the one or more miR-200 family members can comprise or consist of (i) miR-200b and miR-429; or (ii) miR-200c and miR-429.

In embodiments of the invention, the one or more miR-200 family members comprise or consist of miR-141 and/or miR-200a.

In embodiments of the invention, the one or more miR-200 family member comprise or consist of miR-429.

In embodiments of the invention, the one or more miR-200 family members do not include the combination miR-200a, miR-200b and miR-429.

In embodiments of the invention, the one or more miR-200 family members do not include miR-200a. In embodiments of the invention, the one or more miR-200 family members do not include miR-200b. In embodiments of the invention, the one or more miR-200 family members do not include miR-200c. In embodiments of the invention, the one or more miR-200 family members do not include miR-141.

Optionally, the one or more miR-200 family members are human miRNAs (e.g., a mature human miR-429).

In further embodiments of the invention, delivering the one or more miR-200 family members to a cell or subject comprises, consists essentially of, or consists of administering the one or more miR-200 family members as mature miRNAs. For example, in representative embodiments, a mature miR-429 is directly administered to the cell or subject.

Nucleic acids and polynucleotides may be introduced into the desired cells by methods known in the art, e.g., transfection, electroporation, microinjection, transduction, cell fusion, DEAE dextran, calcium phosphate precipitation, lipofection (lysosome fusion), nanoparticle delivery systems (e.g., a nanogel), use of a gene gun, or a nucleic acid vector transporter (see, e.g., Wu et al., J. Biol. Chem. 267:963 (1992); Wu et al., J. Biol. Chem. 263:14621 (1988); and Hartmut et al., Canadian Patent Application No. 2,012,311, filed Mar. 15, 1990).

In various embodiments, a cationic oligopeptide (e.g., WO95/21931), peptides derived from nucleic acid binding proteins (e.g., WO96/25508), and/or a cationic polymer (e.g., WO95/21931) can be used to introduce a nucleic acid or polynucleotide into a cell or subject.

It is also possible to introduce a nucleic acid or polynucleotide into a cell or subject as naked nucleic acid (see U.S. Pat. Nos. 5,693,622, 5,589,466 and 5,580,859). Receptor-mediated nucleic acid delivery approaches can also be used (Curiel et al., Hum. Gene Ther. 3:147 (1992); Wu et al., J. Biol. Chem. 262:4429 (1987)).

The miRNA(s) can be delivered to the cell or subject transiently or stably. For example, transient delivery or expression of the miRNA(s) can be achieved, e.g., with lipofection, microinjection, or nanoparticle delivery. Gene delivery vectors encoding the miRNAs can be used to provide stable expression.

Vector DNA can be introduced into prokaryotic or eukaryotic cells via conventional transformation or transfection techniques. As used herein, the terms "transformation" and "transfection" refer to a variety of art-recognized techniques for introducing foreign nucleic acids (e.g., DNA and RNA) into a host cell, including, but are not limited to, calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al., Molecular Cloning: A Laboratory Manual 2nd Ed. (Cold Spring Harbor, N.Y., 1989), and other laboratory manuals.

If stable integration is desired, often only a small fraction of cells (in particular, mammalian cells) integrate the foreign DNA into their genome. In order to identify and select integrants, a nucleic acid that encodes a selectable marker (e.g., resistance to antibiotics) can be introduced into the host cells along with the nucleic acid of interest. Preferred selectable markers include those that confer resistance to drugs, such as G418, hygromycin and methotrexate. Nucleic acids encoding a selectable marker can be introduced into a host cell on the same vector as that comprising the nucleic acid of interest or can be introduced on a separate vector. Cells stably transfected with the introduced nucleic acid can be identified by drug selection (e.g., cells that have incorporated the selectable marker gene will survive, while the other cells die).

According to certain embodiments, the one or more miR-200 family members can be targeted to ovarian cancer cells in vivo. Methods of targeting delivery vehicles, including liposomes, viral vector and nanoparticle systems are known in the art. For example, a liposome, nanoparticle or viral vector can be directed to a particular target cell or tissue by using a targeting agent, such as an antibody, a soluble receptor or ligand. Targeting liposomes are described, for example, in Ho et al., Biochemistry 25:5500 (1986); Ho et al., J. Biol. Chem. 262:13979 (1987); Ho et al, J. Biol. Chem. 262:13973 (1987); and U.S. Pat. No. 4,957,735 to Huang et al.). Enveloped viral vectors can be modified to deliver a nucleic acid molecule to a target cell by modifying or substituting an envelope protein such that the virus infects a specific cell type (i.e., pseudotyping). In adenoviral vectors, the gene encoding the attachment fibers can be modified to encode a protein domain that binds to a cell-specific receptor.

In addition, the targeting moiety can be, without limitation, an organic or inorganic molecule, a peptide, peptide mimetic, protein, antibody, aptamer, growth factor, enzyme, lectin, antigen or immunogen, virus, viral vector, receptor, ligand (e.g., folic acid), a toxin, a polynucleotide, carbohydrate, sugar, lipid, glycolipids, nucleoprotein, glycoprotein, lipoprotein, steroid, hormone, chemoattractant, cytokine, chemokine, a drug, and the like.

In embodiments of the invention, the targeting moiety is a peptide, e.g., a RGD peptide ligand that targets to tumor neovasculature. The targeting moiety can further target the erythropoietin-producing hepatocellular A2 (EphA2) receptor. An example of such a peptide comprises, consists essentially of, or consists of the amino acid sequence YSAYPDS-VPMMSC (SEQ ID NO:11). Other possibilities for targeting to ovarian cancer cells include an antibody (or portion thereof) that recognizes a cell surface protein, e.g., the mesenchymal markers vimentin, fibronectin or N-cadherin, the epithelial marker E-cadherin, or a tumor marker such as CA-125, HE4 or a cancer testis antigen (e.g., GAGE, MAGE, LAGE, NY-ESO-1). Peptide or nucleic acid aptamers can also be used to target ovarian cancer cells. For example, oligonucleotides can be engineered through repeated rounds of in vitro selection (e.g., SELEX) to generate nucleic acid aptamers with high affinity for specific targets on ovarian cancer cells.

Pharmaceutical Compositions

As a further aspect, the invention provides pharmaceutical formulations, which may comprise any of the reagents discussed herein in a pharmaceutically acceptable carrier.

By "pharmaceutically acceptable" it is meant a material that is not biologically or otherwise undesirable, i.e., the material can be administered to a subject without causing any undesirable biological effects such as toxicity.

The formulations of the invention can optionally comprise medicinal agents, pharmaceutical agents, carriers, adjuvants, dispersing agents, diluents, and the like.

The miRNAs and vectors encoding miRNAs of the invention can be formulated for administration in a pharmaceutical carrier in accordance with known techniques. See, e.g., Remington, The Science And Practice of Pharmacy ($9^{th}$ Ed. 1995). In the manufacture of a pharmaceutical formulation according to the invention, the miRNA or vector (including the physiologically acceptable salts thereof) is typically admixed with, inter alia, an acceptable carrier. The carrier can be a solid or a liquid, or both, and is preferably formulated with the miRNA as a unit-dose formulation, for example, a tablet, which can contain from 0.01 or 0.5% to 95% or 99% by weight of the miRNA or vector. One or more miRNAs or vectors can be incorporated in the formulations of the invention, which can be prepared by any of the well-known techniques of pharmacy.

Non-limiting examples of formulations of the invention include those suitable for oral, rectal, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intracranial, intrathecal, and inhalation administration, administration to the liver by intraportal delivery, as well as direct organ injection (e.g., into the liver, into a limb, into the brain or spinal cord for delivery to the central nervous system, into the pancreas, or into a tumor or the tissue surrounding a tumor). The most suitable route in any given case will depend on the nature and severity of the condition being treated and on the nature of the particular compound which is being used. In some embodiments, it may be desirable to deliver the formulation locally to avoid any side effects associated with systemic administration. For example, local administration can be accomplished by direct injection at the desired treatment site, by introduction intravenously at a site near a desired treatment site (e.g., into a vessel that feeds a treatment site). In certain embodiments, the formulation can be a slow release formulation, e.g., in the form of a slow release depot.

For injection, the carrier will typically be a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

For oral administration, the compound can be administered in solid dosage forms, such as capsules, tablets, and powders, or in liquid dosage forms, such as elixirs, syrups, and suspensions. Compounds can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the one or more miRNAs or vectors, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising a compound of the invention, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is pharmaceutically acceptable can be employed in sufficient quantity to emulsify the compound or salt in an aqueous carrier. One such useful emulsifying agent is phosphatidyl choline.

Formulations suitable for rectal administration are preferably presented as unit dose suppositories. These can be prepared by admixing the compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, Tyle, *Pharm. Res.* 3:318 (1986)) and typically take the form of an optionally buffered aqueous solution of the compound. Suitable formulations comprise citrate or bis\tris buffer (pH 6) or ethanol/water and contain from 0.1 to 0.2M of the compound.

The compound can alternatively be formulated for nasal administration or otherwise administered to the lungs of a subject by any suitable means, e.g., administered by an aerosol suspension of respirable particles comprising the compound, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising the compound can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the compound can likewise be produced with any solid particulate medicament aerosol generator, by techniques known in the pharmaceutical art.

Alternatively, one can administer the compound in a local rather than systemic manner, for example, in a depot or sustained-release formulation.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same can be incorporated into lipid vesicles. In such an instance, due to the water solubility of the compound or salt, the compound or salt will be substantially entrained within the hydrophilic center or core of the liposomes. The lipid layer employed can be of any conventional composition and can either contain cholesterol or can be cholesterol-free. When the compound or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

In a representative embodiment, a polynucleotide can be entrapped in a lipid particle bearing positive charges on its surface and, optionally, tagged with antibodies against cell surface antigens of the target tissue (Mizuno et al., *No Shinkei Geka* 20:547 (1992); PCT publication WO 91/06309; Japanese patent application 1047381; and European patent publication EP-A-43075). Exemplary targeting moieties are as described elsewhere herein.

Liposomes that consist of amphiphilic cationic molecules are useful as non-viral vectors for nucleic acid delivery in vitro and in vivo (reviewed in Crystal, Science 270:404 (1995); Blaese et al., Cancer Gene Ther. 2:291 (1995); Behr et al., Bioconjugate Chem. 5:382 (1994); Remy et al., Bioconjugate Chem. 5:647 (1994); and Gao et al., Gene Therapy 2:710 (1995)). The positively charged liposomes are believed to complex with negatively charged nucleic acids via electrostatic interactions to form lipid:nucleic acid complexes. The lipid:nucleic acid complexes have several advantages as nucleic acid transfer vectors. Unlike viral vectors, the lipid:nucleic acid complexes can be used to transfer expression cassettes of essentially unlimited size. Since the complexes lack proteins, they can evoke fewer immunogenic and inflammatory responses. Moreover, they cannot replicate or recombine to form an infectious agent and have low integration frequency. A number of publications have demonstrated that amphiphilic cationic lipids can mediate nucleic acid delivery in vivo and in vitro (Felgner et al., Proc. Natl. Acad. Sci. USA 84:7413 (1987); Loeffler et al., Meth. Enzymol. 217:599 (1993); Felgner et al., J. Biol. Chem. 269:2550 (1994)).

Several groups have reported the use of amphiphilic cationic lipid:nucleic acid complexes for in vivo transfection both in animals and in humans (reviewed in Gao et al., Gene Therapy 2:710 (1995); Zhu et al., Science 261:209 (1993); and Thierry et al., Proc. Natl. Acad. Sci. USA 92:9742 (1995)). U.S. Pat. No. 6,410,049 describes a method of preparing cationic lipid:nucleic acid complexes that have a prolonged shelf life.

The liposomal formulations comprising the compounds disclosed herein or salts thereof, can be lyophilized to produce a lyophilizate which can be reconstituted with a pharmaceutically acceptable carrier, such as water, to regenerate a liposomal suspension.

miRNAs, polynucleotides, nucleic acids, vectors and the like can also be delivered to a cell in vitro, ex vivo or in vivo using nanoparticle delivery systems (e.g., a nanogel). Exemplary nanoparticles include, but are not limited to, nanospheres (including polymer nanospheres), microspheres (including polymer micelles), dendrimers, quantum dots, gold nanoshells, nanocrystals, colloidal gold, nanoemulsions, nanogels, silver nanoparticles, silica nanoparticles, and the like.

Suitable nanogels include hydrogels (e.g., hyaluronic acid nanogels), polyethylene glycol-polyethylenimine (PEG-PEI) nanogels, poly(alkylacrylamide) nanogels, and the like. Other illustrative nanogels include those disclosed in WO 2010/005741, which describes a crosslinked polymer particle comprising the active agent non-covalently associated with the nanogel. In representative embodiments, the crosslinked polymer particle comprises poly(N-isopropylmethacrylamide) and N,N'-methylenebis(acrylamide). In particular embodiments, the nanogel further comprises a cross-linked polymer shell comprising a functionalization agent, wherein the crosslinked polymer shell is disposed substantially around the crosslinked polymer particle. According to this embodiment, the crosslinked polymer shell can comprise, without limitation, poly(N-isopropylmethacrylamide), N,N'-methylenebis(acrylamide) and aminopropylmethacrylamide.

The nanogel can further comprise a targeting moiety, as described elsewhere herein.

In particular embodiments, the compound is administered to the subject in a treatment effective amount, as that term is defined herein. Dosages of pharmaceutically active compounds can be determined by methods known in the art, see, e.g., *Remington's Pharmaceutical Sciences* (Maack Publishing Co., Easton, Pa.). The therapeutically effective dosage of any specific compound will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the compound, including the cases where a salt is employed. Toxicity concerns at the higher level can restrict intravenous dosages to a lower level such as up to about 10 mg/kg, with all weights being calculated based upon the weight of the compound, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Particular dosages are about 1 µmol/kg to 50 µmol/kg, and more particularly to about 22 µmol/kg and to 33 µmol/kg of the compound for intravenous or oral administration, respectively.

The present invention is more particularly described in the following examples that are intended as illustrative only since numerous modifications and variations therein will be apparent to those skilled in the art.

Example 1

Materials and Methods

Cell Lines.

The OVCAR3 cell line was originally established from the ascites of a patient with poorly differentiated papillary epithelial OC [Hamilton et al., Cancer Res 1985, 45:3668-76]. The OVCAR3 cell line was obtained from the American Type Culture Collection (Manassas, Va.). The HEY cell line was derived from a patient with moderately differentiated papillary cystadenocarcinoma of the ovary [Buick et al., Cancer Res 1985, 45:3668-76]. The HEY cell line was kindly provided by Gordon Mills, Department of Molecular Therapeutics, University of Texas, MD Anderson Cancer Center.

microRNA Transfection.

$6 \times 10^4$ cells per well were seeded in 24-well plates. After 24 h, cells were transfected with 30 nM of miR-429 and miR-320 miRNA oligonucleotides (Ambion, Austin, Tex.) using Lipofectamine 2000 reagent (Invitrogen, Carlsbad, Calif.). The Ambion Pre-miRNA Precursor Negative Control was used as a control. Three days after transfection, cells were split and transfected again. This process was repeated every 3 days until 21 days when cells were assayed for response.

RNA Quantification.

Total RNA was extracted from cells using the miRVana miRNA isolation kit (Ambion). MicroRNA expression was carried our using TaqMan microRNA assays (Applied Biosystems, Carlsbad, Calif.) with human U6 as the endogenous control. For mRNA quantitation, RNA (4.0 μg) was reversed transcribed into cDNA using the Superscript III First-strand Synthesis System (Invitrogen) according to the manufacturer's instructions using sequence specific primers. Real-time PCR was performed using Power SYBR Green PCR Master Mix (Bio-Rad, Hercules, Calif.) and data normalized to glyceraldehydes-3-phosphate-dehydrogenase (GAPDH). Each transfection experiment was carried out in triplicate with 3 PCR reactions performed per transfection. The PCR results were analyzed by 1-way Analysis of Variance (ANOVA) and the Newman-Keuls-Student t test. A p value of <0.05 was considered significant.

Microarray Analyses.

Microarray analyses were performed using the Affymetrix system (HG-U133 Plus 2.0; Santa Clara, Calif.) as previously described [Bowen et al., BMC Med Genomics 2009, 2:71]. Briefly, the expression data were analyzed using MAS 5.0 Statistical Algorithm encoded in the Affymetrix Expression Console application. The expression values were normalized across samples by Z-score calculation using Spotfire Decision Site software. ANOVA was used to identify genes whose expression was significantly different ($p<0.015$; fold change $\geq 1.5$ or fold change 1.5) between HEY cells transfected with miR-429 and the negative control. Gene enrichment analyses were carried out using GeneGO (http://www.genego.com/) gene ontology software.

Invasion, Migration, Wound Healing and Anchorage-Independent Growth Assays.

For the migration and invasion assays, $2.5 \times 10^3$ overnight serum starved cells in serum-free media were added to the top chambers of trans-well plates (8 μm pore size; BD, Franklin Lakes, N.J.) and media containing 10% fetal calf serum (FCS) were added to the bottom chambers. After 8-12 h, the non-migrating (top) cells were removed and the invading (bottom) cells were counted. All assays were done in triplicate. For the wound-healing assay, $2.5 \times 10^5$ cells were seeded into six-well plates. After 24 h, a wound was incised, detached cells removed and fresh media added. Photos were taken after 8 hrs to monitor the invasion of cells into the wounded area.

Anchorage independent growth was examined using Cell Biolab's (San Diego, Calif.) soft agar kit according to the manufacturer's protocol. Briefly, 5,000 cells were grown in a 0.3% low melting temperature agar matrix. After 8 days of incubation, the agar matrix was solubilized, cells stained and absorbance recorded at 520 nm. The optical density (OD) was measured in a 96-well plate reader using a 485/520 nm filter set.

Example 2

Figure 1A:
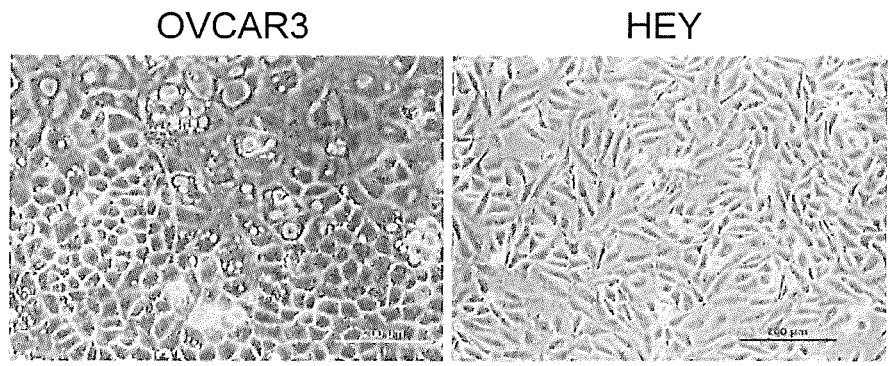
FIGS. 1A-C. OVCAR3 and HEY cells display distinct morphological and molecular profiles. (A) OVCAR3 cells display a rounded/cobblestone, epithelial-like morphology while HEY cells display a more elongated morphology characteristic of mesenchymal cells. (B) Expression levels of mRNAs encoding ZEB2, ZEB1, E-cadherin, N-cadherin, FN1 (fibronectin) and VIM (vimentin) in HEY cells normalized to mean expression levels present in OVCAR3 cells.
Figure 1B:
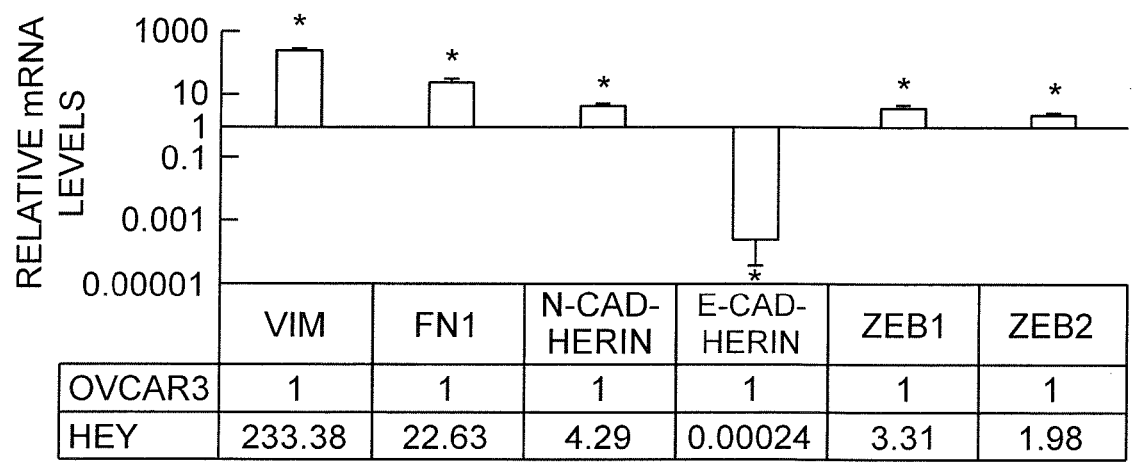
Figure 1C:
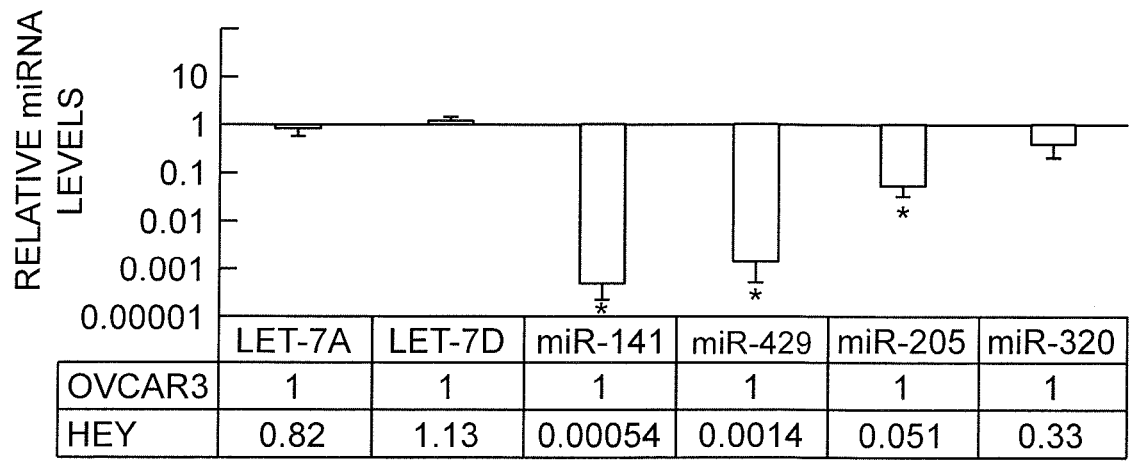

OVCAR3 and HEY Cells Display Molecular Profiles Consistent with their Distinct Epithelial and Mesenchymal-Like Morphologies To explore a possible role of microRNAs in ovarian cancer EMT and metastasis, we compared the expression levels of 2 miR-200 family microRNAs (miR-141, miR-429), miR-205, let-7a, let-7d and miR-320 between two OC cell lines. OVCAR3 cells display a rounded/cobblestone, epithelial-like morphology while HEY cells display a more elongated morphology characteristic of mesenchymal cells (FIG. 1A) and have been shown to be significantly more invasive and metastatic than OVCAR3 cells in xenograft mouse models [Shaw et al., Mol Ther 2004; 10:1032-42]. Consistent with these morphological distinctions, we found that the mesenchymal markers vimentin (VIM), fibronectin (FN1) and N-cadherin are all more highly expressed in HEY cells relative to OVCAR3 cells (FIG. 1B). In addition, the epithelial marker, E-cadherin, is expressed at significantly lower levels while the repressors of E-cadherin, ZEB1 and ZEB2, are expressed at significantly higher levels in HEY cells relative to OVCAR3 cells (FIG. 1B). Consistent with the hypothesis that the down-regulation of members of the miRNA-200 family and miR-205 may contribute to EMT in ovarian cancer, we found that miR-141, miR-429 and miR-205 are all expressed at significantly lower levels in HEY cells relative to OVCAR3 cells ($p<0.01$, FIG. 1C). No significant changes were observed in levels of let-7a, let-7d or mir-320 ($p>0.01$; FIG. 1C).

Example 3

Overexpression of miR-429 in HEY Cells Induces Morphological and Molecular Changes Consistent with a Mesenchymal-to-Epithelial Transition (MET)

To test the hypothesis that miR-200 family members may be involved in EMT in OC, we compared the effect of ectopic expression of miR-429 in HEY cells relative to miR-320 and a control RNA sequence not homologous to any known microRNA. While miR-320 expression is reported to have an inhibitory effect on cell proliferation [Schaar et al., Exp Hematol 2009; 37:245-55], it has not been previously implicated in EMT. MiR-429 was selected to represent the miR-200 family because it is predicted to have the largest number of putative target sites in ZEB1 and ZEB2 mRNAs (ZEB1 mRNA contains 5 putative biding sites for miR-429, 3 for miR-141 and 1 for miR-205; ZEB2 mRNA contains 6 putative binding sites for miR-429, 3 for miR-141 and 2 for miR-205). We reasoned that if down-regulation of miR-429 contributes to EMT in OC, expression of miR-429 in the more mesenchymal-like HEY cells might be expected to induce changes characteristic of MET while expression of the control sequences should have little or no effect.

The results presented in FIG. 2A demonstrate that expression of miR-429 induced HEY cells to undergo a morphological change from an elongated, spindle-shaped, mesenchymal phenotype to a more rounded, epithelial-like phenotype. In contrast, no change in morphology was detected in HEY cells transfected with miR-320 or with the negative control microRNA sequence. Consistent with the miR-429 induced change in morphology, we observed a significant decrease in levels of ZEB1 and ZEB2 and a concomitant increase in levels of E-cadherin (FIG. 2B). Again, no significant change was detected in cells transfected with miR-320 or with the negative control microRNA.

Example 4

Overexpression of miR-429 in HEY Cells Induces Global Changes in Gene Expression Consistent with MET To more fully characterize the molecular effects of miR-429 expression in HEY cells, we conducted a comparative microarray profiling analysis (Affymetrix HG-U133 Plus 2.0). The results demonstrate that 296 genes were significantly down regulated and 373 genes were significantly up regulated in the miR429-transfected cells compared with controls (p<0.015; fold change≥1.5 or fold change≥1.5; Table 2). Included among those genes displaying significant changes in expression after miR-429 transfection were the mesenchymal markers ZEB 1 and VCAN (versican) [Soltermann et al, Clin Cancer Res 2008; 14:7430-7] (both downregulated) and the epithelial markers TSPAN13 (tetraspanin-13) [Huang et al., J Cancer Res Clin Oncol 2007; 133:761-9], CAV2 (caveolin 2) [Moreno-Bueno et al., Cancer Res 2006; 66:9543-56], DSP (desmoplakin) [Sarrió et al., Cancer Res 2008; 68:989-97] and EPCAM (epithelial cell adhesion molecule) [Huang et al., Cancer Res 2007; 67:11147-57] (all up-regulated). While ZEB 2 was found to be significantly down regulated in our RT-PCR analysis, it did not display a significant change in expression in our microarray analysis. We attribute this inconsistency to the fact that microarray is less sensitive than RT-PCR in the detection of changes in low abundant transcripts [Meyer et al., Biotechniques 2004; 36:618-20].

The fact that <9% of genes significantly down regulated in expression are predicted targets of miR-429 (3% predicted by Target Scan -http://www.targetscan.org/; 9% by miRanda -http://www.microrna.org/microrna/home.do) (Table 3) suggests that the vast majority of the observed molecular changes were indirect effects of miR-429 overexpression. Gene ontology (GO) analysis of the 669 genes displaying significant changes in expression in the miR-429 transfected cells demonstrated a significant enrichment for genes associated with functions typically associated with EMT and metastasis (e.g., significant over-representation of genes involved in EMT, cell differentiation/development, cell junction and cell adhesion, FIG. 3 and Tables 4-6).

Example 5

Overexpression of miR-429 in HEY Cells Induces Changes in Functional Characteristics Consistent with MET To further explore the effects of ectopic expression of miR-429 in HEY cells, we looked for changes in cellular functions frequently associated with EMT. For example, ovarian and other types of cancer cells undergoing EMT typically display increased motility/migration and invasiveness. To determine if expression of miR-429 resulted in a reduction in the migratory ability of transfected HEY cells, we monitored the effect of serum-induced migration of cells using chamber assays. The results demonstrate that miR-429 transfected HEY cells migrated through pores >2-fold slower than the negative controls (FIG. 4A). Relative invasiveness was also measured by monitoring serum-induced invasion through a matrigel layer. The results indicate a >5-fold decrease in invasion in miR-429 transfected HEY cells relative to controls (FIG. 4A). The reduced migration of HEY cells over expressing miR-429 was further confirmed using the wound healing assay (FIG. 4B).

Anchorage-independent growth is another characteristic of mesenchymal cells and is considered a hallmark of cellular transformation [Takeyama et al., Cancer Lett 2010; 96:216-24]. We tested anchorage-independent growth of HEY cells transfected with miR-429 relative to controls. After 8 days incubation in soft agar, the miR-429 transfected cells displayed a significant suppression of anchorage-independent growth relative to controls consistent with miR-429 induced MET (FIG. 4C).

Collectively, our results are consistent with the hypothesis that miR-200 family microRNAs and miR-429, in particular, are directly involved in EMT and the promotion of OC metastasis.

Example 6 miR-429 Transfection Increases Sensitivity of HEY Cells to Cisplatin

Cultures of the mesenchymal HEY cells were transfected with a negative control (NC) miRNA or miR-429 using Lipofectamine 2000 (Invitrogen) and treated with increasing concentrations of cisplatin. (0.1, 0.5, 1, 3, 5, 7, 10, 15, 20, 30, 50 µM). Sensitivity to cisplatin increased significantly in the presence of miR-429 as compared with the negative control (FIG. 5; $IC_{50}$ 4.6 vs. 8.7 for experimental and control groups, respectively).

Example 7

Ectopic Expression of miR-200 Family in Animal Models of Ovarian Cancer

A mouse model of ovarian cancer is used to evaluate the effectiveness of upregulation of miR-200 family members (miR-141, miR-200a, miR-200b, miR-200c, miR-205 and/or miR-429) altogether, individually or in combination (e.g., miR-200c/miR-141 or miR-200a/miR-200b/miR-429), for treatment of ovarian cancer as well as the ability to reduce metastasis (including malignant ascites) and/or recurrence/disease progression, to prolong progression-free survival and/or overall survival and/or to enhance sensitivity to chemotherapy. One suitable mouse model is the mouse xenograft model in which human ovarian cancer cells are delivered subcutaneously or into the peritoneum of nude mice. Other models of ovarian cancer include a mouse model with concurrent homozygous knockout of p53 and Rb. Further, transgenic mice in which the 5' upstream regulatory sequences of the mouse misiir (Müllerian inhibitory substance type II receptor) gene were used to target expression of the SV40 large T antigen (TAg) specifically to the female reproductive epithelium, developed ovarian carcinomas with metastatic spread by three months of age (Vanderhyden et al., Animal models of ovarian cancer. Reproductive Biology and Endocrinology 2003, 1:67).

One or more miR-200 family members are transiently delivered by the intravenous or intraperitoneal route to two groups of mice, while the other two groups receive a negative control miRNA. Within the experimental and control treatments, one group will receive a chemotherapeutic agent (e.g., a platinum drug and/or a taxane) 0, 24, 48 or 72 hours after administration of the miRNA(s) and one does not. Transient delivery of the miRNA(s) can be achieved by any suitable means, e.g., by lipofection (see, Example 1) or by a targeted nanogel (see, e.g., Dickerson et al., BMC Cancer 2010, 10:10; WO 2010/005741).

The animals are monitored and evaluated for regression of the tumors and/or extent of metastasis (including malignant ascites), with and without chemotherapy. Animals showing a partial or complete response to treatment can be further monitored for recurrence/disease progression. Progression-free survival and/or overall survival can also be determined.

The foregoing is illustrative of the present invention, and is not to be construed as limiting thereof, The invention is defined by the following claims, with equivalents of the claims to be included therein.

All publications, patent applications, patents and other references cited herein are incorporated by reference in their entireties for the teachings relevant to the sentence and/or paragraph in which the reference is presented.

TABLE 2

List of genes differentially expressed between miR-429 and negative control microRNA transfected HEY cells. Shown are fold changes and significance values.

| Gene Symbol | Fold change (miR-429 transfected HEY cells relative to negative controls) | p-value |
|---|---|---|
| LOC284561 | −38.32 | 0.0010 |
| NOC2L | −26.91 | 0.0083 |
| PAPPA2 | −23.75 | 0.0008 |
| COLEC12 | −16.11 | 0.0010 |
| TLR1 | −15.24 | 0.0101 |
| SNORA68 | −14.52 | 0.0129 |
| PCOTH | −13.93 | 0.0035 |
| CDO1 | −13.45 | 0.0008 |
| SYF2 | −12.64 | 0.0020 |
| GAS7 | −12.55 | 0.0035 |
| ALDH1L2 | −11.31 | 0.0041 |
| SHANK2 | −10.85 | 0.0084 |
| LOC286178 | −10.56 | 0.0115 |
| HORMAD1 | −10.48 | 0.0005 |
| SLC24A3 | −10.20 | 0.0003 |
| C12orf39 | −10.06 | 0.0010 |
| LOC401497 | −9.19 | 0.0002 |
| ANKRD23 | −7.62 | 0.0077 |
| hCG_1654703 | −7.46 | 0.0139 |
| LOC158381 | −7.31 | 0.0136 |
| PSAT1 | −6.92 | 0.0021 |
| ASNS | −6.82 | 0.0029 |
| MARS | −6.59 | 0.0081 |
| SLC27A4 | −6.23 | 0.0024 |
| C12orf55 | −6.06 | 0.0100 |
| TMEM201 | −5.58 | 0.0082 |
| SLC7A11 | −5.46 | 0.0018 |
| F2RL2 | −5.35 | 0.0030 |
| SH3PXD2B | −5.13 | 0.0065 |
| GLT8D2 | −4.76 | 0.0148 |
| PCK2 | −4.44 | 0.0004 |
| NAV3 | −4.35 | 0.0050 |
| OSTM1 | −4.35 | 0.0025 |
| SLC1A4 | −4.32 | 0.0048 |
| EPHB1 | −4.06 | 0.0039 |
| CCND2 | −4.03 | 0.0001 |
| CHST10 | −4.03 | 0.0041 |
| GART | −3.94 | 0.0076 |
| PHGDH | −3.78 | 0.0115 |
| FOXP3 | −3.76 | 0.0044 |
| PYGO1 | −3.61 | 0.0009 |
| SESN2 | −3.61 | 0.0085 |
| ANK2 | −3.58 | 0.0032 |
| ERN1 | −3.51 | 0.0035 |
| ABCF2 | −3.48 | 0.0058 |
| ASAM | −3.48 | 0.0042 |
| CDC42EP1 | −3.48 | 0.0076 |
| C17orf51 | −3.46 | 0.0139 |
| JDP2 | −3.46 | 0.0015 |
| MGC16121 | −3.46 | 0.0008 |
| CCDC148 | −3.39 | 0.0054 |
| KIAA1853 | −3.32 | 0.0023 |
| GRK4 | −3.14 | 0.0022 |
| LMO4 | −3.14 | 0.0081 |
| HIF3A | −3.12 | 0.0147 |
| CCDC152 | −3.10 | 0.0054 |
| PTPN13 | −3.10 | 0.0021 |
| LOC148987 | −3.07 | 0.0079 |
| MRAP | −3.05 | 0.0031 |
| MERTK | −3.03 | 0.0139 |
| SLC1A5 | −3.01 | 0.0055 |
| BCHE | −2.93 | 0.0080 |
| RGMB | −2.89 | 0.0139 |
| EXOSC6 | −2.87 | 0.0001 |
| GPATCH4 | −2.87 | 0.0028 |
| INTS4 | −2.81 | 0.0093 |
| CLGN | −2.79 | 0.0123 |
| TMEM156 | −2.79 | 0.0130 |
| CYCS | −2.73 | 0.0089 |
| FLJ34077 | −2.73 | 0.0118 |
| GLIPR1 | −2.73 | 0.0066 |
| LOC148189 | −2.69 | 0.0133 |
| CBS | −2.68 | 0.0101 |
| DDR2 | −2.68 | 0.0027 |
| LRP4 | −2.66 | 0.0022 |
| SYT11 | −2.66 | 0.0043 |
| CDKAL1 | −2.64 | 0.0141 |
| HS6ST3 | −2.64 | 0.0098 |
| ZNF30 | −2.62 | 0.0112 |
| AARS | −2.57 | 0.0058 |
| CXCL3 | −2.57 | 0.0025 |
| KLHL13 | −2.57 | 0.0088 |
| SGSH | −2.57 | 0.0141 |
| MARS2 | −2.50 | 0.0124 |
| C6orf105 | −2.48 | 0.0063 |
| HSPA9 | −2.48 | 0.0003 |
| LOC439949 | −2.48 | 0.0023 |
| CCNJ | −2.45 | 0.0109 |
| PITX2 | −2.45 | 0.0118 |
| RPL22L1 | −2.45 | 0.0113 |
| YARS | −2.45 | 0.0082 |
| SRCAP | −2.43 | 0.0092 |
| C11orf57 | −2.41 | 0.0005 |
| GALNT12 | −2.39 | 0.0005 |

TABLE 3

Only ~9% of genes down regulated in miR-429 transfected HEY cells are predicted targets of miR-429. (A) MiRanda predicted targets of miR-429 that were down regulated in miR-429 transfected HEY cells (9% of all down regulated genes). (B) Targetscan predicted targets of miR-429 that were down regulated in miR-429 transfected HEY cells (3% of all down regulated genes).

| Gene | Fold-change | t-test |
|---|---|---|
| A | | |
| ALDH1L2 | −11.31 | 0.0041 |
| PSAT1 | −6.92 | 0.0021 |
| MARS | −6.59 | 0.0081 |
| NAV3 | −4.35 | 0.0050 |
| OSTM1 | −4.35 | 0.0025 |
| GART | −3.94 | 0.0076 |
| PTPN13 | −3.10 | 0.0021 |
| BCHE | −2.93 | 0.0080 |
| GALNT12 | −2.39 | 0.0005 |
| TIGD1 | −2.38 | 0.0006 |
| TSGA14 | −2.33 | 0.0075 |
| B3GALNT2 | −2.16 | 0.0005 |
| EIF2B5 | −2.10 | 0.0086 |
| GREM1 | −2.10 | 0.0055 |
| RDH10 | −2.08 | 0.0133 |
| SHMT2 | −2.04 | 0.0001 |
| ZNF697 | −1.91 | 0.0114 |
| WDR43 | −1.88 | 0.0125 |
| LOC339290 | −1.87 | 0.0114 |
| ZBTB24 | −1.87 | 0.0145 |
| STARD13 | −1.78 | 0.0040 |
| ZEB1 | −1.78 | 0.0018 |
| CFL2 | −1.75 | 0.0142 |
| LDLRAD3 | −1.74 | 0.0063 |
| VCAN | −1.66 | 0.0135 |
| DPY19L1 | −1.64 | 0.0033 |

TABLE 3-continued

Only ~9% of genes down regulated in miR-429 transfected HEY cells are predicted targets of miR-429. (A) MiRanda predicted targets of miR-429 that were down regulated in miR-429 transfected HEY cells (9% of all down regulated genes). (B) Targetscan predicted targets of miR-429 that were down regulated in miR-429 transfected HEY cells (3% of all down regulated genes).

| Gene | Fold-change | t-test |
| --- | --- | --- |
| PRTG | −1.61 | 0.0043 |
| DNAJB4 | −1.53 | 0.0081 |
| B | | |
| OSTM1 | −4.35 | 0.0025 |
| TSGA14 | −2.33 | 0.0075 |
| EIF2B5 | −2.10 | 0.0086 |
| RDH10 | −2.08 | 0.0133 |
| ZNF697 | −1.91 | 0.0114 |
| SENP5 | −1.80 | 0.0007 |
| STARD13 | −1.78 | 0.0040 |
| ZEB1 | −1.78 | 0.0018 |
| CFL2 | −1.75 | 0.0142 |
| DPY19L1 | −1.64 | 0.0033 |

TABLE 4

Differentially expressed genes displaying significant enrichment in the GO (gene ontology) classification "cellular components" between miR-429 and negative control microRNA transfected HEY cells.

| GO classification (cellular components) | gene name | enrichment P value |
| --- | --- | --- |
| Adherens junction | ARHGEF12 | 3.485E−3 |
| Adherens junction | ARHGEF2 | 3.485E−3 |
| Adherens junction | BAIAP2 | 3.485E−3 |
| Adherens junction | ENAH | 3.485E−3 |
| Adherens junction | ETV4 | 3.485E−3 |
| Adherens junction | FYN | 3.485E−3 |
| Adherens junction | LAMA3 | 3.485E−3 |
| Adherens junction | LPP | 3.485E−3 |
| Adherens junction | NEDD9 | 3.485E−3 |
| Adherens junction | OXTR | 3.485E−3 |
| Adherens junction | PPP1R9B | 3.485E−3 |
| Adherens junction | PTK2B | 3.485E−3 |
| Adherens junction | SORBS1 | 3.485E−3 |
| Adherens junction | SYNM | 3.485E−3 |
| Adherens junction | TJP2 | 3.485E−3 |
| Adherens junction | WASF2 | 3.485E−3 |
| Cell-cell junction | ARHGEF2 | 5.254E−3 |
| Cell-cell junction | B4GALT1 | 5.254E−3 |
| Cell-cell junction | BVES | 5.254E−3 |
| Cell-cell junction | CDC42BPA | 5.254E−3 |
| Cell-cell junction | COL13A1 | 5.254E−3 |
| Cell-cell junction | FMNL2 | 5.254E−3 |
| Cell-cell junction | INADL | 5.254E−3 |
| Cell-cell junction | LAMA3 | 5.254E−3 |
| Cell-cell junction | OXTR | 5.254E−3 |
| Cell-cell junction | SORBS1 | 5.254E−3 |
| Cell-cell junction | TJP2 | 5.254E−3 |
| Cell junction | ARHGEF12 | 2.232E−2 |
| Cell junction | ARHGEF2 | 2.232E−2 |
| Cell junction | B4GALT1 | 2.232E−2 |
| Cell junction | BAIAP2 | 2.232E−2 |
| Cell junction | BVES | 2.232E−2 |
| Cell junction | CDC42BPA | 2.232E−2 |
| Cell junction | COL13A1 | 2.232E−2 |
| Cell junction | DNMBP | 2.232E−2 |
| Cell junction | DST | 2.232E−2 |
| Cell junction | ENAH | 2.232E−2 |
| Cell junction | ETV4 | 2.232E−2 |
| Cell junction | FYN | 2.232E−2 |
| Cell junction | INADL | 2.232E−2 |
| Cell junction | LAMA3 | 2.232E−2 |
| Cell junction | LIMA1 | 2.232E−2 |
| Cell junction | LPP | 2.232E−2 |
| Cell junction | MAP3K1 | 2.232E−2 |
| Cell junction | NEDD9 | 2.232E−2 |
| Cell junction | OXTR | 2.232E−2 |
| Cell junction | PPP1R9B | 2.232E−2 |
| Cell junction | PTK2B | 2.232E−2 |
| Cell junction | SHANK2 | 2.232E−2 |
| Cell junction | SIPA1L1 | 2.232E−2 |
| Cell junction | SORBS1 | 2.232E−2 |
| Cell junction | SYNGAP1 | 2.232E−2 |
| Cell junction | SYNM | 2.232E−2 |
| Cell junction | SYT12 | 2.232E−2 |
| Cell junction | TJP2 | 2.232E−2 |
| Cell junction | WASF2 | 2.232E−2 |
| Cell-substrate junction | BAIAP2 | 2.458E−2 |
| Cell-substrate junction | DST | 2.458E−2 |
| Cell-substrate junction | ENAH | 2.458E−2 |
| Cell-substrate junction | ETV4 | 2.458E−2 |
| Cell-substrate junction | FYN | 2.458E−2 |
| Cell-substrate junction | LAMA3 | 2.458E−2 |
| Cell-substrate junction | LPP | 2.458E−2 |
| Cell-substrate junction | NEDD9 | 2.458E−2 |
| Cell-substrate junction | PTK2B | 2.458E−2 |
| Cell-substrate junction | SORBS1 | 2.458E−2 |
| Cell-substrate junction | WASF2 | 2.458E−2 |
| Laminin-1 complex | LAMA3 | 2.502E−2 |
| Laminin-1 complex | LAMA4 | 2.502E−2 |
| Laminin-1 complex | SDC2 | 2.502E−2 |
| Laminin-1 complex | SLPI | 2.502E−2 |
| Cell-cell adherens junction | DSP | 3.073E−2 |
| Cell-cell adherens junction | LAMA3 | 3.073E−2 |
| Cell-cell adherens junction | OXTR | 3.073E−2 |
| Cell-cell adherens junction | PLEKHA7 | 3.073E−2 |
| Cell-cell adherens junction | SORBS1 | 3.073E−2 |
| Extracellular matrix | ADAMTS12 | 3.928E−2 |
| Extracellular matrix | ADAMTS18 | 3.928E−2 |
| Extracellular matrix | ANGPTL4 | 3.928E−2 |
| Extracellular matrix | COL13A1 | 3.928E−2 |
| Extracellular matrix | COL6A1 | 3.928E−2 |
| Extracellular matrix | DMP1 | 3.928E−2 |
| Extracellular matrix | DSPP | 3.928E−2 |
| Extracellular matrix | DST | 3.928E−2 |
| Extracellular matrix | F3 | 3.928E−2 |
| Extracellular matrix | FYN | 3.928E−2 |
| Extracellular matrix | HBEGF | 3.928E−2 |
| Extracellular matrix | IGFBP3 | 3.928E−2 |
| Extracellular matrix | KLK2 | 3.928E−2 |
| Extracellular matrix | LAMA3 | 3.928E−2 |
| Extracellular matrix | LAMA4 | 3.928E−2 |
| Extracellular matrix | LMCD1 | 3.928E−2 |
| Extracellular matrix | MAP3K1 | 3.928E−2 |
| Extracellular matrix | MMP1 | 3.928E−2 |
| Extracellular matrix | PLAT | 3.928E−2 |
| Extracellular matrix | SDC2 | 3.928E−2 |
| Extracellular matrix | SLPI | 3.928E−2 |
| Extracellular matrix | SPINT2 | 3.928E−2 |
| Extracellular matrix | TGFB2 | 3.928E−2 |
| Extracellular matrix | THBS1 | 3.928E−2 |
| Extracellular matrix | VCAN | 3.928E−2 |
| Cytoskeleton | AKAP12 | 4.656E−2 |
| Cytoskeleton | ANK2 | 4.656E−2 |
| Cytoskeleton | ANXA11 | 4.656E−2 |
| Cytoskeleton | ARHGEF12 | 4.656E−2 |
| Cytoskeleton | ARHGEF2 | 4.656E−2 |
| Cytoskeleton | ARRB1 | 4.656E−2 |
| Cytoskeleton | BAIAP2 | 4.656E−2 |
| Cytoskeleton | BRIP1 | 4.656E−2 |
| Cytoskeleton | BYSL | 4.656E−2 |
| Cytoskeleton | C13orf15 | 4.656E−2 |
| Cytoskeleton | C21orf33 | 4.656E−2 |
| Cytoskeleton | CALM1 | 4.656E−2 |
| Cytoskeleton | CAPG | 4.656E−2 |

TABLE 4-continued

Differentially expressed genes displaying significant enrichment in the GO (gene ontology) classification "cellular components" between miR-429 and negative control microRNA transfected HEY cells.

| GO classification (cellular components) | gene name | enrichment P value |
|---|---|---|
| Cytoskeleton | CASP9 | 4.656E-2 |
| Cytoskeleton | CFL2 | 4.656E-2 |
| Cytoskeleton | CLIC5 | 4.656E-2 |
| Cytoskeleton | CSRP3 | 4.656E-2 |
| Cytoskeleton | CYCS | 4.656E-2 |
| Cytoskeleton | DCTN1 | 4.656E-2 |
| Cytoskeleton | DNM3 | 4.656E-2 |
| Cytoskeleton | DNMBP | 4.656E-2 |
| Cytoskeleton | DSP | 4.656E-2 |
| Cytoskeleton | DST | 4.656E-2 |
| Cytoskeleton | DUSP1 | 4.656E-2 |
| Cytoskeleton | ENAH | 4.656E-2 |
| Cytoskeleton | ERN1 | 4.656E-2 |
| Cytoskeleton | FGD4 | 4.656E-2 |
| Cytoskeleton | FMNL2 | 4.656E-2 |
| Cytoskeleton | FNBP1 | 4.656E-2 |
| Cytoskeleton | FYN | 4.656E-2 |
| Cytoskeleton | GAS7 | 4.656E-2 |
| Cytoskeleton | GPR4 | 4.656E-2 |
| Cytoskeleton | H2AFY | 4.656E-2 |
| Cytoskeleton | HIP1 | 4.656E-2 |
| Cytoskeleton | KIF2A | 4.656E-2 |
| Cytoskeleton | KITLG | 4.656E-2 |
| Cytoskeleton | LIMA1 | 4.656E-2 |
| Cytoskeleton | LITAF | 4.656E-2 |
| Cytoskeleton | MAP3K1 | 4.656E-2 |
| Cytoskeleton | MTUS1 | 4.656E-2 |
| Cytoskeleton | MYO6 | 4.656E-2 |
| Cytoskeleton | MYO7A | 4.656E-2 |
| Cytoskeleton | MYOF | 4.656E-2 |
| Cytoskeleton | NDRG1 | 4.656E-2 |
| Cytoskeleton | NEDD9 | 4.656E-2 |
| Cytoskeleton | PLCG2 | 4.656E-2 |
| Cytoskeleton | PLEKHA1 | 4.656E-2 |
| Cytoskeleton | PLEKHA2 | 4.656E-2 |
| Cytoskeleton | PPP1R9B | 4.656E-2 |
| Cytoskeleton | PROCR | 4.656E-2 |
| Cytoskeleton | PTPN13 | 4.656E-2 |
| Cytoskeleton | PTPN14 | 4.656E-2 |
| Cytoskeleton | RASSF5 | 4.656E-2 |
| Cytoskeleton | S100A8 | 4.656E-2 |
| Cytoskeleton | S100A9 | 4.656E-2 |
| Cytoskeleton | SHANK2 | 4.656E-2 |
| Cytoskeleton | SIPA1L1 | 4.656E-2 |
| Cytoskeleton | SLC1A4 | 4.656E-2 |
| Cytoskeleton | SLC7A11 | 4.656E-2 |
| Cytoskeleton | SORBS1 | 4.656E-2 |
| Cytoskeleton | SPTBN1 | 4.656E-2 |
| Cytoskeleton | SYNM | 4.656E-2 |
| Cytoskeleton | UACA | 4.656E-2 |
| Cytoskeleton | WASF2 | 4.656E-2 |
| Cytoskeleton | WIPF2 | 4.656E-2 |
| Focal adhesion | ARHGEF12 | 8.487E-2 |
| Focal adhesion | BAIAP2 | 8.487E-2 |
| Focal adhesion | ENAH | 8.487E-2 |
| Focal adhesion | ETV4 | 8.487E-2 |
| Focal adhesion | FYN | 8.487E-2 |
| Focal adhesion | LPP | 8.487E-2 |
| Focal adhesion | NEDD9 | 8.487E-2 |
| Focal adhesion | PDPK1 | 8.487E-2 |
| Focal adhesion | PTK2B | 8.487E-2 |
| Focal adhesion | SORBS1 | 8.487E-2 |
| Focal adhesion | WASF2 | 8.487E-2 |

TABLE 5

Differentially expressed genes displaying significant enrichment in the GO classification "biological process" between miR-429 and negative control microRNA transfected HEY cells.

| GO classification (biological process) | gene name | enrichment P value |
|---|---|---|
| cell projection organization | MYO7A | 3.748E-13 |
| anatomical structure development | GLI3 | 4.258E-12 |
| anatomical structure development | LRP4 | 4.258E-12 |
| cell differentiation | AMH | 2.040E-11 |
| cell differentiation | ANGPTL4 | 2.040E-11 |
| cell differentiation | CLGN | 2.040E-11 |
| cell differentiation | COL13A1 | 2.040E-11 |
| cell differentiation | CSRP3 | 2.040E-11 |
| cell differentiation | DLX1 | 2.040E-11 |
| cell differentiation | DSPP | 2.040E-11 |
| cell differentiation | ECSCR | 2.040E-11 |
| cell differentiation | EFNA5 | 2.040E-11 |
| cell differentiation | ELF3 | 2.040E-11 |
| cell differentiation | EPAS1 | 2.040E-11 |
| cell differentiation | ETV6 | 2.040E-11 |
| cell differentiation | FNBP1 | 2.040E-11 |
| cell differentiation | FZD5 | 2.040E-11 |
| cell differentiation | GADD45B | 2.040E-11 |
| cell differentiation | GAS7 | 2.040E-11 |
| cell differentiation | HIP1 | 2.040E-11 |
| cell differentiation | KDM3A | 2.040E-11 |
| cell differentiation | KIF2A | 2.040E-11 |
| cell differentiation | L1CAM | 2.040E-11 |
| cell differentiation | NRP1 | 2.040E-11 |
| cell differentiation | PAPPA2 | 2.040E-11 |
| cell differentiation | PPP1R9B | 2.040E-11 |
| cell differentiation | PSME4 | 2.040E-11 |
| cell differentiation | PTK2B | 2.040E-11 |
| cell differentiation | SEMA5A | 2.040E-11 |
| cell differentiation | SH3PXD2B | 2.040E-11 |
| cell differentiation | SIM1 | 2.040E-11 |
| cell differentiation | SOX9 | 2.040E-11 |
| cell differentiation | SRRM4 | 2.040E-11 |
| multicellular organismal development | ANGPTL4 | 6.012E-11 |
| multicellular organismal development | ATR | 6.012E-11 |
| multicellular organismal development | B3GNT5 | 6.012E-11 |
| multicellular organismal development | BST1 | 6.012E-11 |
| multicellular organismal development | BVES | 6.012E-11 |
| multicellular organismal development | CELSR2 | 6.012E-11 |
| multicellular organismal development | CLGN | 6.012E-11 |
| multicellular organismal development | COL13A1 | 6.012E-11 |
| multicellular organismal development | CSRP3 | 6.012E-11 |
| multicellular organismal development | DLX1 | 6.012E-11 |
| multicellular organismal development | DSPP | 6.012E-11 |
| multicellular organismal development | ECSCR | 6.012E-11 |
| multicellular organismal development | EFNA5 | 6.012E-11 |
| multicellular organismal development | ELF3 | 6.012E-11 |
| multicellular organismal development | EPAS1 | 6.012E-11 |
| multicellular organismal development | FNBP1 | 6.012E-11 |
| multicellular organismal development | FYN | 6.012E-11 |
| multicellular organismal development | FZD5 | 6.012E-11 |
| multicellular organismal development | GADD45B | 6.012E-11 |
| multicellular organismal development | GAS7 | 6.012E-11 |
| multicellular organismal development | GREM1 | 6.012E-11 |
| multicellular organismal development | HOXA13 | 6.012E-11 |
| multicellular organismal development | KIF2A | 6.012E-11 |
| multicellular organismal development | KLF3 | 6.012E-11 |
| multicellular organismal development | L1CAM | 6.012E-11 |
| multicellular organismal development | LIMD1 | 6.012E-11 |
| multicellular organismal development | LSM14A | 6.012E-11 |
| multicellular organismal development | NRP1 | 6.012E-11 |
| multicellular organismal development | PIM1 | 6.012E-11 |
| multicellular organismal development | PITX2 | 6.012E-11 |
| multicellular organismal development | PPP1R9B | 6.012E-11 |
| multicellular organismal development | PRTG | 6.012E-11 |
| multicellular organismal development | PSME4 | 6.012E-11 |
| multicellular organismal development | SEMA5A | 6.012E-11 |
| multicellular organismal development | SIM1 | 6.012E-11 |
| multicellular organismal development | SORL1 | 6.012E-11 |
| multicellular organismal development | VCAN | 6.012E-11 |
| multicellular organismal development | WLS | 6.012E-11 |
| multicellular organismal development | ZNF260 | 6.012E-11 |

TABLE 6

Differentially expressed genes displaying significant enrichment in the GO classification "biological process network" between miR-429 and negative control microRNA transfected HEY cells.

| GO classification (process network) | gene name | enrichment P value |
|---|---|---|
| Cell adhesion__Synaptic contact | BAIAP2 | 5.045E−05 |
| Cell adhesion__Synaptic contact | CNTN1 | 5.045E−05 |
| Cell adhesion__Synaptic contact | EFNA5 | 5.045E−05 |
| Cell adhesion__Synaptic contact | EPHB1 | 5.045E−05 |
| Cell adhesion__Synaptic contact | EPHB2 | 5.045E−05 |
| Cell adhesion__Synaptic contact | FYN | 5.045E−05 |
| Cell adhesion__Synaptic contact | L1CAM | 5.045E−05 |
| Cell adhesion__Synaptic contact | NCAM1 | 5.045E−05 |
| Cell adhesion__Synaptic contact | NLGN3 | 5.045E−05 |
| Cell adhesion__Synaptic contact | SDC2 | 5.045E−05 |
| Cell adhesion__Synaptic contact | SHANK2 | 5.045E−05 |
| Cell adhesion__Synaptic contact | SYNGAP1 | 5.045E−05 |
| Cell adhesion__Synaptic contact | SYT11 | 5.045E−05 |
| Cell adhesion__Synaptic contact | SYT12 | 5.045E−05 |
| Cell adhesion__Synaptic contact | YWHAH | 5.045E−05 |
| Cell adhesion__Attractive and repulsive receptors | ARHGEF12 | 7.846E−04 |
| Cell adhesion__Attractive and repulsive receptors | CFL2 | 7.846E−04 |
| Cell adhesion__Attractive and repulsive receptors | COL13A1 | 7.846E−04 |
| Cell adhesion__Attractive and repulsive receptors | EFNA5 | 7.846E−04 |
| Cell adhesion__Attractive and repulsive receptors | ENAH | 7.846E−04 |
| Cell adhesion__Attractive and repulsive receptors | EPHB1 | 7.846E−04 |
| Cell adhesion__Attractive and repulsive receptors | EPHB2 | 7.846E−04 |
| Cell adhesion__Attractive and repulsive receptors | FYN | 7.846E−04 |
| Cell adhesion__Attractive and repulsive receptors | L1CAM | 7.846E−04 |
| Cell adhesion__Attractive and repulsive receptors | NCAM1 | 7.846E−04 |
| Cell adhesion__Attractive and repulsive receptors | NEO1 | 7.846E−04 |
| Cell adhesion__Attractive and repulsive receptors | NRP1 | 7.846E−04 |
| Cell adhesion__Attractive and repulsive receptors | RASA1 | 7.846E−04 |
| Cell adhesion__Attractive and repulsive receptors | SEMA5A | 7.846E−04 |
| Cell adhesion__Leucocyte chemotaxis | ARHGEF12 | 6.066E−04 |
| Cell adhesion__Leucocyte chemotaxis | CALM1 | 6.066E−04 |
| Cell adhesion__Leucocyte chemotaxis | CFL2 | 6.066E−04 |
| Cell adhesion__Leucocyte chemotaxis | CXCL2 | 6.066E−04 |
| Cell adhesion__Leucocyte chemotaxis | CXCL3 | 6.066E−04 |
| Cell adhesion__Leucocyte chemotaxis | CYTH3 | 6.066E−04 |
| Cell adhesion__Leucocyte chemotaxis | F2RL2 | 6.066E−04 |
| Cell adhesion__Leucocyte chemotaxis | FYN | 6.066E−04 |
| Cell adhesion__Leucocyte chemotaxis | ITGA9 | 6.066E−04 |
| Cell adhesion__Leucocyte chemotaxis | LPAR1 | 6.066E−04 |
| Cell adhesion__Leucocyte chemotaxis | LPAR3 | 6.066E−04 |
| Cell adhesion__Leucocyte chemotaxis | OXTR | 6.066E−04 |
| Cell adhesion__Leucocyte chemotaxis | PDPK1 | 6.066E−04 |
| Cell adhesion__Leucocyte chemotaxis | PLCG2 | 6.066E−04 |
| Cell adhesion__Leucocyte chemotaxis | PTK2B | 6.066E−04 |
| Cell adhesion__Leucocyte chemotaxis | RASSF5 | 6.066E−04 |
| Cytoskeleton__Actin filaments | CAPG | 3.132E−02 |
| Cytoskeleton__Actin filaments | CDC42BPA | 3.132E−02 |
| Cytoskeleton__Actin filaments | CFL2 | 3.132E−02 |
| Cytoskeleton__Actin filaments | DCTN1 | 3.132E−02 |
| Cytoskeleton__Actin filaments | DST | 3.132E−02 |
| Cytoskeleton__Actin filaments | FYN | 3.132E−02 |
| Cytoskeleton__Actin filaments | MYO1D | 3.132E−02 |
| Cytoskeleton__Actin filaments | MYO6 | 3.132E−02 |
| Cytoskeleton__Actin filaments | MYO7A | 3.132E−02 |
| Cytoskeleton__Actin filaments | NEDD9 | 3.132E−02 |
| Cytoskeleton__Actin filaments | SPTBN1 | 3.132E−02 |
| Cytoskeleton__Actin filaments | WASF2 | 3.132E−02 |
| Cytoskeleton__Regulation of cytoskeleton rearrangement | ARHGEF2 | 4.046E−02 |
| Cytoskeleton__Regulation of cytoskeleton rearrangement | CDC42BPA | 4.046E−02 |
| Cytoskeleton__Regulation of cytoskeleton rearrangement | CFL2 | 4.046E−02 |
| Cytoskeleton__Regulation of cytoskeleton rearrangement | DST | 4.046E−02 |
| Cytoskeleton__Regulation of cytoskeleton rearrangement | FGD4 | 4.046E−02 |
| Cytoskeleton__Regulation of cytoskeleton rearrangement | NEDD9 | 4.046E−02 |
| Cytoskeleton__Regulation of cytoskeleton rearrangement | PREX1 | 4.046E−02 |
| Cytoskeleton__Regulation of cytoskeleton rearrangement | SPTBN1 | 4.046E−02 |
| Cytoskeleton__Regulation of cytoskeleton rearrangement | WASF2 | 4.046E−02 |
| Cytoskeleton__Regulation of cytoskeleton rearrangement | YWHAH | 4.046E−02 |
| Development__Neurogenesis:Axonal guidance/Synaptogenesis | ARHGEF12 | 1.365E−05 |
| Development__Neurogenesis:Axonal guidance/Synaptogenesis | BAIAP2 | 1.365E−05 |
| Development__Neurogenesis:Axonal guidance/Synaptogenesis | CALM1 | 1.365E−05 |
| Development__Neurogenesis:Axonal guidance/Synaptogenesis | CFL2 | 1.365E−05 |
| Development__Neurogenesis:Axonal guidance/Synaptogenesis | DCTN1 | 1.365E−05 |
| Development__Neurogenesis:Axonal guidance/Synaptogenesis | DPYSL3 | 1.365E−05 |
| Development__Neurogenesis:Axonal guidance/Synaptogenesis | EFNA5 | 1.365E−05 |
| Development__Neurogenesis:Axonal guidance/Synaptogenesis | ENAH | 1.365E−05 |
| Development__Neurogenesis:Axonal guidance/Synaptogenesis | EPHB1 | 1.365E−05 |
| Development__Neurogenesis:Axonal guidance/Synaptogenesis | EPHB2 | 1.365E−05 |
| Development__Neurogenesis:Axonal guidance/Synaptogenesis | FYN | 1.365E−05 |
| Development__Neurogenesis:Axonal guidance/Synaptogenesis | GAS7 | 1.365E−05 |
| Development__Neurogenesis:Axonal guidance/Synaptogenesis | L1CAM | 1.365E−05 |
| Development__Neurogenesis:Axonal guidance/Synaptogenesis | NCAM1 | 1.365E−05 |
| Development__Neurogenesis:Axonal guidance/Synaptogenesis | NEO1 | 1.365E−05 |
| Development__Neurogenesis:Axonal guidance/Synaptogenesis | NRP1 | 1.365E−05 |
| Development__Neurogenesis:Axonal guidance/Synaptogenesis | PLCG2 | 1.365E−05 |
| Development__Neurogenesis:Axonal guidance/Synaptogenesis | SDC2 | 1.365E−05 |
| Development__Neurogenesis:Axonal guidance/Synaptogenesis | SEMA5A | 1.365E−05 |
| Development__Neurogenesis:Axonal guidance/Synaptogenesis | WASF2 | 1.365E−05 |
| Development__Neurogenesis:Axonal guidance/Synaptogenesis | YWHAH | 1.365E−05 |
| Development__Blood vessel morphogenesis | ANGPTL4 | 3.074E−04 |
| Development__Blood vessel morphogenesis | EDN1 | 3.074E−04 |
| Development__Blood vessel morphogenesis | EGLN1 | 3.074E−04 |
| Development__Blood vessel morphogenesis | EPAS1 | 3.074E−04 |
| Development__Blood vessel morphogenesis | F2RL2 | 3.074E−04 |
| Development__Blood vessel morphogenesis | FGFR1 | 3.074E−04 |
| Development__Blood vessel morphogenesis | FOXF1 | 3.074E−04 |
| Development__Blood vessel morphogenesis | HBEGF | 3.074E−04 |
| Development__Blood vessel morphogenesis | KLK2 | 3.074E−04 |
| Development__Blood vessel morphogenesis | L1CAM | 3.074E−04 |
| Development__Blood vessel morphogenesis | LPAR1 | 3.074E−04 |

TABLE 6-continued

Differentially expressed genes displaying significant enrichment in the GO classification "biological process network" between miR-429 and negative control microRNA transfected HEY cells.

| GO classification (process network) | gene name | enrichment P value |
|---|---|---|
| Development_Blood vessel morphogenesis | LPAR3 | 3.074E-04 |
| Development_Blood vessel morphogenesis | MAP3K1 | 3.074E-04 |
| Development_Blood vessel morphogenesis | NRP1 | 3.074E-04 |
| Development_Blood vessel morphogenesis | OXTR | 3.074E-04 |
| Development_Blood vessel morphogenesis | PDE1C | 3.074E-04 |
| Development_Blood vessel morphogenesis | PDPK1 | 3.074E-04 |
| Development_Blood vessel morphogenesis | PITX2 | 3.074E-04 |
| Development_Blood vessel morphogenesis | PGK1 | 3.074E-04 |
| Development_Blood vessel morphogenesis | PLAT | 3.074E-04 |
| Development_Blood vessel morphogenesis | TGFA | 3.074E-04 |
| Development_Regulation of angiogenesis | ANGPTL4 | 6.241E-04 |
| Development_Regulation of angiogenesis | EDN1 | 6.241E-04 |
| Development_Regulation of angiogenesis | EFNA5 | 6.241E-04 |
| Development_Regulation of angiogenesis | EPHB1 | 6.241E-04 |
| Development_Regulation of angiogenesis | EPHB2 | 6.241E-04 |
| Development_Regulation of angiogenesis | F2RL2 | 6.241E-04 |
| Development_Regulation of angiogenesis | GLI3 | 6.241E-04 |
| Development_Regulation of angiogenesis | GLMN | 6.241E-04 |
| Development_Regulation of angiogenesis | HBEGF | 6.241E-04 |
| Development_Regulation of angiogenesis | MALT1 | 6.241E-04 |
| Development_Regulation of angiogenesis | OXTR | 6.241E-04 |
| Development_Regulation of angiogenesis | PDPK1 | 6.241E-04 |
| Development_Regulation of angiogenesis | PITX2 | 6.241E-04 |
| Development_Regulation of angiogenesis | RASA1 | 6.241E-04 |
| Development_Regulation of angiogenesis | SEMA5A | 6.241E-04 |
| Development_Regulation of angiogenesis | TGFB2 | 6.241E-04 |
| Development_Regulation of angiogenesis | TGFBR1 | 6.241E-04 |
| Development_Regulation of angiogenesis | THBS1 | 6.241E-04 |
| Development_Regulation of angiogenesis | ZEB1 | 6.241E-04 |

We claim:

1. A method of sensitizing an ovarian cancer to a cytotoxic therapy, the method comprising delivering a modified miR-429, wherein the modified miR-429 comprises a seed sequence, AAUACUG, and further wherein the modified miR-429 comprises one or more nucleotide substitutions and/or deletions in the nucleotide sequence of SEQ ID NO:5 outside of the seed sequence, to a mammalian subject in need thereof in an amount effective to sensitize the ovarian cancer to cytotoxic therapy.

2. The method of claim 1, wherein the method further comprises detecting a level of one or more miR-200 family members in ovarian cancer tissue from the subject that is below a reference value prior to administering the modified miR-429 to the subject.

3. The method of claim 1, wherein the method further comprises detecting cells having a mesenchymal phenotype in ovarian cancer tissue from the subject prior to administering the modified miR-429 to the subject.

4. The method of claim 1, wherein the method further comprises administering a cytotoxic therapy prior to, concurrently with and/or after administration of the modified miR-429.

5. The method of claim 4, wherein the cytotoxic therapy comprises a chemotherapy agent.

6. The method of claim 4, wherein the cytotoxic therapy comprises radiation therapy.

7. The method of claim 1, wherein the modified miR-429 is transiently delivered by lipofection, a nanoparticle delivery system, or a nanogel delivery system.

8. The method of claim 7, wherein the method comprises administration of a nanogel delivering the modified miR-429 to the subject, wherein the nanogel comprises a crosslinked polymer particle comprising the active agent non-covalently associated with the nanogel.

9. The method of claim 8, wherein the crosslinked polymer particle comprises poly(N-isopropylmethacrylamide) and N,N'-methylenebis(acrylamide).

10. The method of claim 8, wherein the nanogel further comprises a cross-linked polymer shell, wherein the crosslinked polymer shell is disposed substantially around the crosslinked polymer particle.

11. The method of claim 10, wherein the crosslinked polymer shell comprises poly(N-isopropylmethacrylamide), N,N'-methylenebis(acrylamide), and aminopropylmethacrylamide.

12. The method of claim 1, wherein a mature modified miR-429 is administered to the subject.

13. The method of claim 1, wherein a human modified miR-429 is delivered.

14. The method of claim 1, wherein the subject is a human subject.

* * * * *

UNITED STATES PATENT AND TRADEMARK OFFICE
CERTIFICATE OF CORRECTION

PATENT NO. : 8,895,509 B2
APPLICATION NO. : 13/989312
DATED : November 25, 2014
INVENTOR(S) : McDonald et al.

It is certified that error appears in the above-identified patent and that said Letters Patent is hereby corrected as shown below:

In the Specification

Column 25, Line 28: Please correct "change 1.5)"
to read -- change $\leq 1.5$) --

Signed and Sealed this
Twenty-first Day of April, 2015

Michelle K. Lee
*Director of the United States Patent and Trademark Office*